Figure 3:
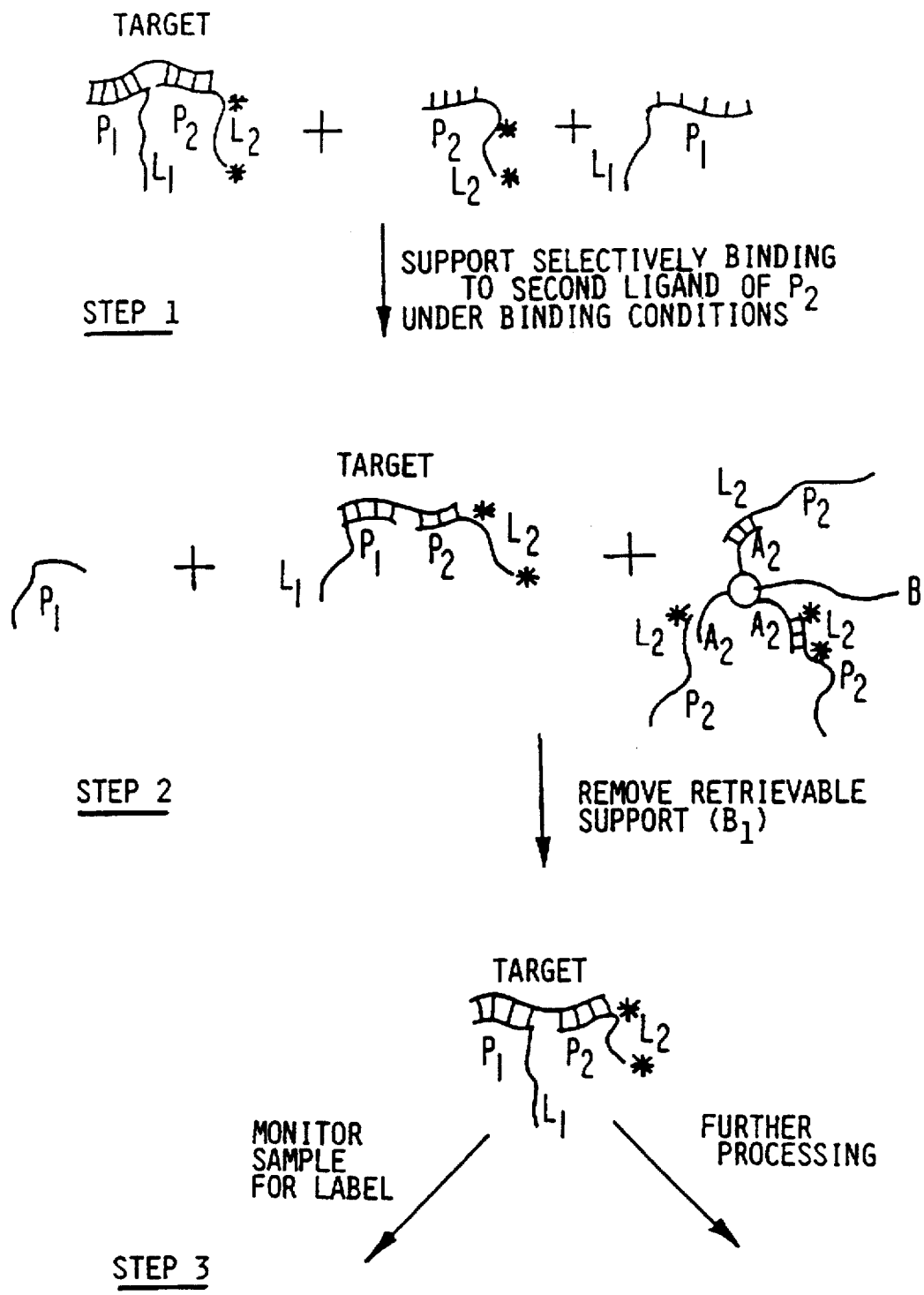

United States Patent [19]

Collins

[11] Patent Number: 5,780,224
[45] Date of Patent: Jul. 14, 1998

[54] TARGET AND BACKGROUND CAPTURE METHODS AND APPARATUS FOR AFFINITY ASSAYS

[75] Inventor: Mark L. Collins, Holden, Mass.

[73] Assignee: AMOCO Corporation, Chicago, Ill.

[21] Appl. No.: 236,877

[22] Filed: Apr. 29, 1994

Related U.S. Application Data

[63] Continuation of Ser. No. 6,804, Jan. 21, 1993, abandoned, which is a continuation of Ser. No. 859,619, Mar. 23, 1992, abandoned, which is a continuation of Ser. No. 550,147, Jul. 9, 1990, abandoned, which is a continuation of Ser. No. 922,155, Oct. 23, 1986, abandoned.

[51] Int. Cl.$^6$ ................................................ C12Q 1/68
[52] U.S. Cl. .............. 435/6; 536/25.4; 536/24.3; 935/77; 935/78
[58] Field of Search .............. 435/6, 810; 536/24.3, 536/25.4; 935/77, 78

[56] References Cited

U.S. PATENT DOCUMENTS

| | | | |
|---|---|---|---|
| 4,672,040 | 6/1987 | Josephson | 436/526 |
| 4,752,566 | 6/1988 | Collins | 435/6 |
| 4,824,776 | 4/1989 | Heller | 435/6 |
| 4,894,325 | 1/1990 | Englehardt | 435/6 |

*Primary Examiner*—Carla J. Myers
*Attorney, Agent, or Firm*—Norval B. Galloway

[57] ABSTRACT

Methods, compositions and instruments for performing affinity assays for target molecules include contacting a sample with a retrievable support capable of forming a substantially homogenous dispersion within a sample medium and reversibly binding to the target molecule. The retrievable support is capable of being separated from the sample medium recapturing the target molecule from other constituents of the sample.

20 Claims, 7 Drawing Sheets

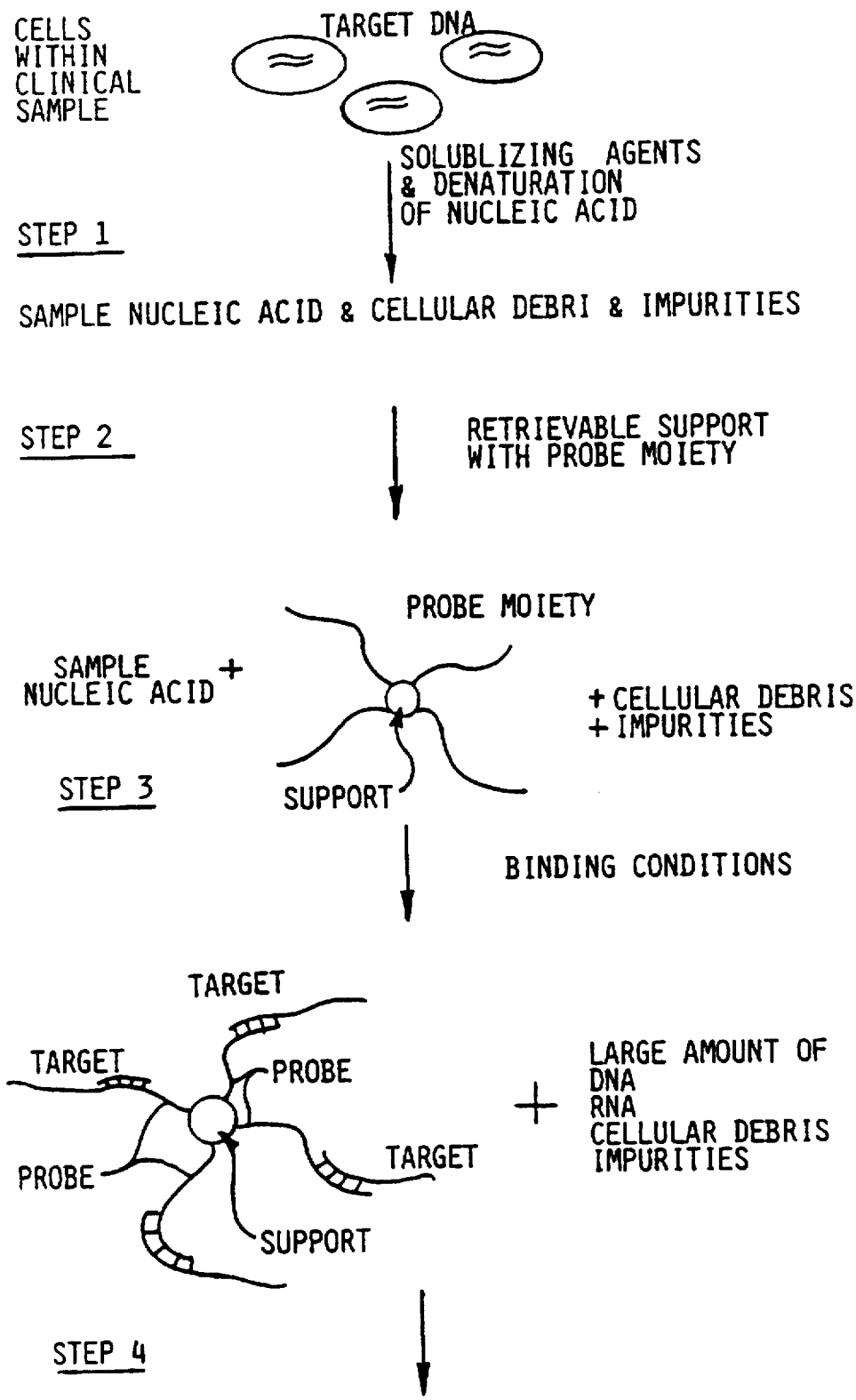

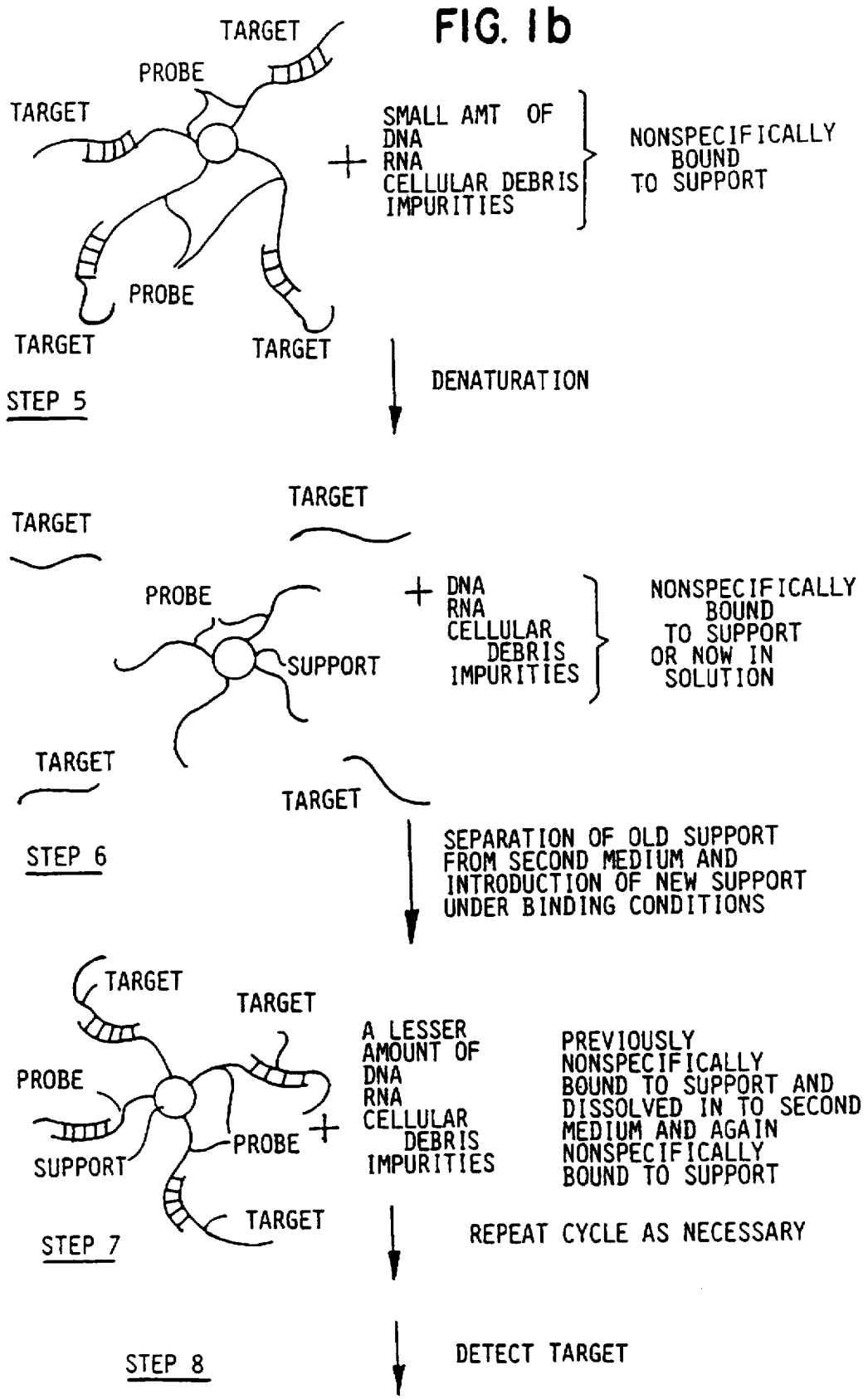

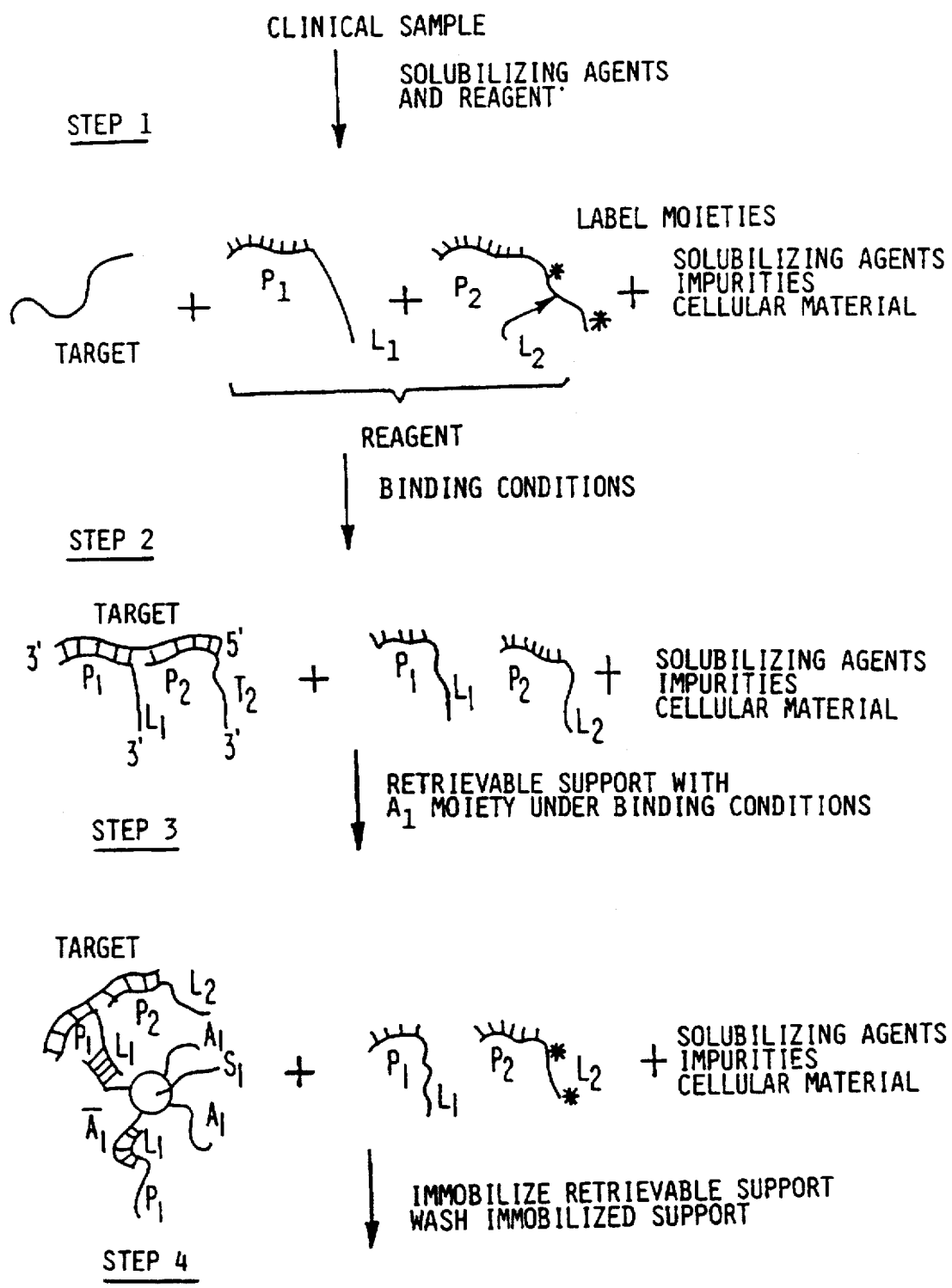

FIG. 2b
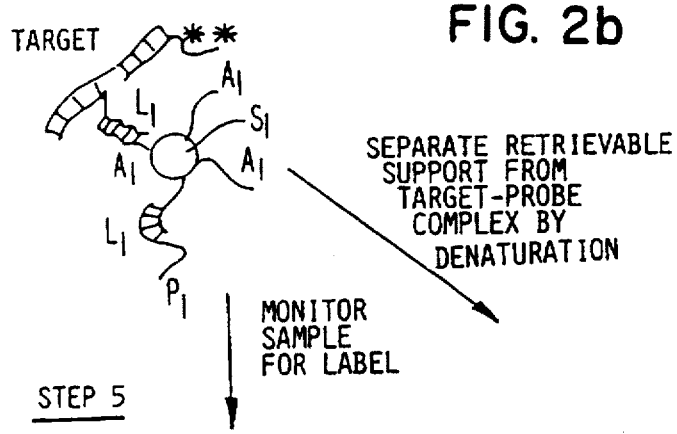
STEP 5
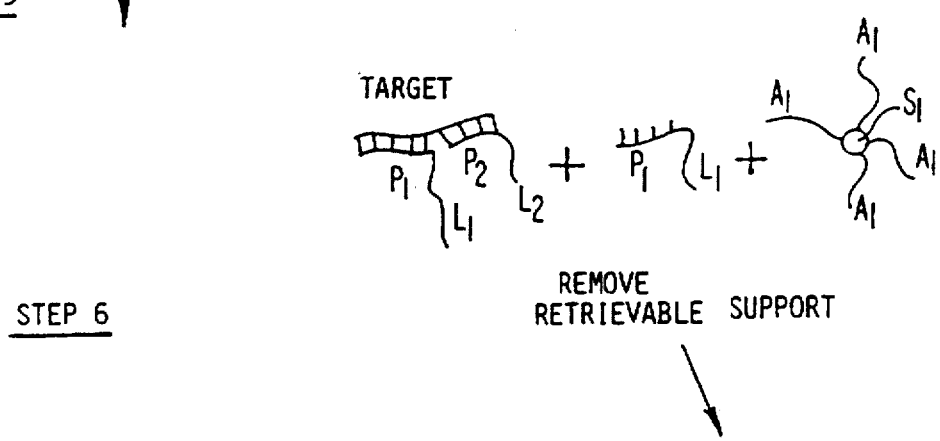
STEP 6
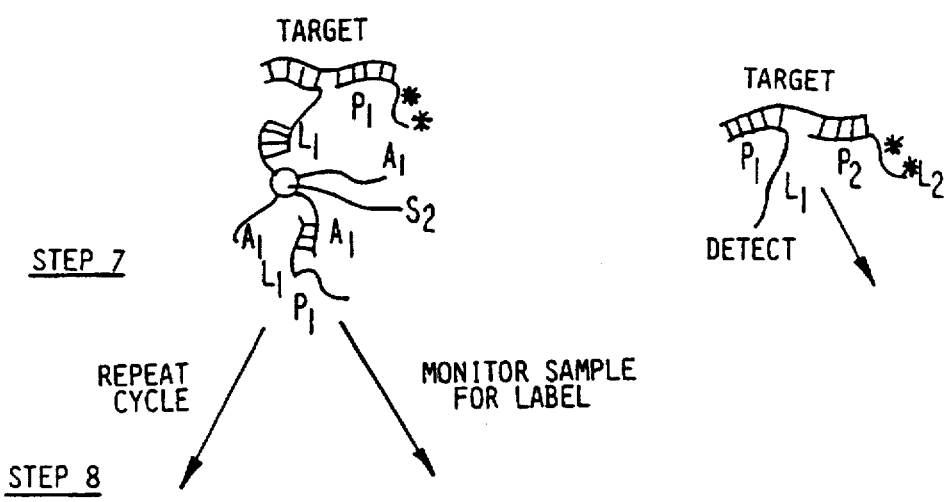
STEP 7
STEP 8

TARGET AND BACKGROUND CAPTURE METHODS AND APPARATUS FOR AFFINITY ASSAYS

This application is a continuation of application Ser. No. 08/006,804, filed Jan. 21, 1993 and now abandoned, which is a continuation of application Ser. No. 07/859,619, filed Mar. 23, 1992 and now abandoned, which is a continuation of application Ser. No. 07/550,147, filed Jul. 9, 1990 and now abandoned, which is a continuation of application Ser. No. 06/922,155, filed Oct. 23, 1986 and now abandoned.

BACKGROUND OF THE INVENTION

The present invention pertains to methods, reagents, compositions, kits, and instruments for use in capturing target molecules. In particular, the present invention relates to methods, reagents, compositions, and kits for capturing deoxyribonucleic acid (DNA) or ribonucleic acid (RNA) from clinical samples. Embodiments of the present invention provide methods for rapid, sensitive detection of nucleic acid targets in clinical samples adaptable to non-radioactive labeling techniques and automation.

The following definitions are provided to facilitate an understanding of the present invention. The term "biological binding pair" as used in the present application refers to any pair of molecules which exhibit natural affinity or binding capacity. For the purposes of the present application, the term "ligand" will refer to one molecule of the biological binding pair and the term "antiligand" or "receptor" will refer to the opposite molecule of the biological binding pair. For example, without limitation, embodiments of the present invention have applications in nucleic acid hybridization assays where the biological binding pair includes two complementary strands of polynucleic acid. One of the strands is designated the ligand and the other strand is designated the antiligand. However, the biological binding pair may include antigens and antibodies, drugs, and drug receptor sites and enzymes and enzyme substrates.

The term "probe" refers to a ligand of known qualities capable of selectively binding to a target antiligand. As applied to nucleic acids, the term "probe" refers to a strand of nucleic acid having a base sequence complementary to a target strand.

The term "label" refers to a molecular moiety capable of detection including, by way of example, without limitation, radioactive isotopes, enzymes, luminescent agents, and dyes. The term "agent" is used in a broad sense, including any molecular moiety which participates in reactions which lead to a detectable response. The term "cofactor" is used broadly to include any molecular moiety which participates in reactions with the agent.

The term "retrievable" is used in a broad sense to describe an entity which can be substantially dispersed within a medium and removed or separated from the medium by immobilization, filtering, partitioning, or the like.

The term "support" when used alone includes conventional supports such as filters and membranes as well as retrievable supports.

The term "reversible," in regard to the binding of ligands and antiligands, means capable of binding or releasing upon imposing changes which do not permanently alter the gross chemical nature of the ligand and antiligand. For example, without limitation, reversible binding would include such binding and release controlled by changes in pH, temperature, and ionic strength which do not destroy the ligand or antiligand. Genetic information is stored in living cells in threadlike molecules of DNA. In vivo, the DNA molecule is a double helix, each strand of which is a chain of nucleotides. Each nucleotide is characterized by one of four bases: adenine (A), guanine (G), thymine (T), and cytosine (C). The bases are complementary in the sense that, due to the orientation of functional groups, certain base pairs attract and bond to each other through hydrogen bonding. Adenine in one strand of DNA pairs with thymine in an opposing complementary strand. Guanine in one strand of DNA pairs with cytosine in an opposing complementary strand. In RNA, the thymine base is replaced by uracil (U) which pairs with cytosine in an opposing complementary strand.

DNA consists of covalently linked chains of deoxyribonucleotides and RNA consists of covalently linked chains of ribonucleotides. The genetic code of a living organism is carried upon the DNA strand in the sequence of the base pairs.

Each nucleic acid is linked by a phosphodiester bridge between the five prime hydroxyl group of the sugar of one nucleotide and the three prime hydroxyl group of the sugar of an adjacent nucleotide. Each linear strand of naturally occurring DNA or RNA has one terminal end having a five prime hydroxyl end and a three prime end. The terminal ends of polynucleotides are often referred to as being five prime termini or three prime termini in reference to the respective free hydroxyl group. Complementary strands of DNA and RNA form antiparallel complexes in which the three prime terminal end of one strand is oriented and bound to the five prime terminal end of the opposing strand.

Nucleic acid hybridization assays are based on the tendency of two nucleic acid strands to pair at complementary regions. Presently, nucleic acid hybridization assays are primarily used to detect and identify unique DNA or RNA base sequences or specific genes in a complete DNA molecule, in mixtures of nucleic acid, or in mixtures of nucleic acid fragments.

The identification of unique DNA or RNA sequences or specific genes within the total DNA or RNA extracted from tissue or culture samples may indicate the presence of physiological or pathological conditions. In particular, the identification of unique DNA or RNA sequences or specific genes, within the total DNA or RNA extracted from human or animal tissue, may indicate the presence of genetic diseases or conditions such as sickle cell anemia, tissue compatibility, cancer and precancerous states, or bacterial or viral infections. The identification of unique DNA or RNA sequences or specific genes within the total DNA or RNA extracted from bacterial cultures or tissue containing bacteria may indicate the presence of antibiotic resistance, toxins, viruses, or plasmids, or provide identification between types of bacteria.

Thus, nucleic acid hybridization assays have great potential in the diagnosis and detection of disease. Further potential exists in agriculture and food processing where nucleic acid hybridization assays may be used to detect plant pathogenesis or toxin-producing bacteria.

One of the most widely used nucleic acid hybridization assay procedures is known as the Southern blot filter hybridization method or simply, the Southern procedure (Southern, E., *J. Mol. Biol.l*, 98,503, 1975). The Southern procedure is used to identify target DNA or RNA sequences. This procedure is generally carried out by immobilizing sample RNA or DNA to nitrocellulose sheets. The immobilized sample RNA or DNA is contacted with radio-labeled probe strands of DNA having a base sequence complementary to the and carrying a radioactive moiety which can be detected. Hybridization between the probe and the sample DNA is allowed to take place.

The hybridization process is generally very specific. The labeled probe will not combine with sample DNA or RNA if the two nucleotide entities do not share substantial complementary base pair organization. Hybridization can take from three to 48 hours depending on given conditions.

However, as a practical matter there is always nonspecific binding of the labeled probe to supports which appears as "background noise" on detection. Background noise reduces the sensitivity of an assay. Unhybridized DNA probe is subsequently washed away. The nitrocellulose sheet is placed on a sheet of X-ray film and allowed, to expose the film. The X-ray film is developed with the exposed areas of the film identifying DNA fragments which have been hybridized to the DNA probe and therefore have the base pair sequence of interest.

The use of radioactive labeling agents in conjunction with Southern assay techniques have allowed the application of nucleic acid assays to clinical samples. Radioactive decay is detectable even in clinical samples containing extraneous proteinaceous and organic material. However, the presence of extraneous proteinaceous and organic material may contribute to nonspecific binding of the probe to the solid support. Moreover, the use of radioactive labeling techniques requires a long exposure time to visualize bands on X-ray film. A typical Southern procedure may require 1 to 7 days for exposure. The use of radioactive labeling agents further requires special laboratory procedures and licenses.

The above problems associated with assays involving radioisotopic labels have led to the development of techniques employing nonisotopic labels. Examples of nonisotopic labels include enzymes, luminescent agents, and dyes. Luminescent labels emit light upon exitation by an external energy source and may be grouped into categories dependent upon the source of the exciting energy, including: radioluminescent labels deriving energy from high energy particles; chemiluminescent labels which obtain energy from chemical reactions; bioluminescent labels wherein the exciting energy is applied in a biological system; and photoluminescent or fluorescent labels which are excitable by units of electromagnetic radiation (photons) of infrared, visual or ultraviolet light. See, generally, Smith et al., *Ann. Clin. Biochem.*, 18:253, 274 (1981).

Nonisotopic assay techniques employing labels excitable by nonradioactive energy sources avoid the health hazards and licensing problems encountered with radioisotopic label assay techniques. Moreover, nonisotopic assay techniques hold promise for rapid detection avoiding the long exposure time associated with the use of X-ray film.

However, nonisotopic assays have not conveyed the sensitivity or specificity to assay procedures necessary to be considered reliable. In luminescent assays, the presence of proteins and other molecules carried in biological samples may cause scattering of the exciting light or may absorb light in the spectrum of emission of the luminescent label, resulting in a quenching of the luminescent probe.

In enzymatic assays, the presence of proteins and other molecules carried in biological samples may interfere with the activity of the enzyme.

Similarly, in colorimetric assays, the change in color may not be detectable over proteins and other materials carried in biological samples.

Embodiments of the present invention are concerned with target and background capture on supports and on retrievable supports including magnetic particles. Magnetic particles have been suggested as supports for the synthesis of organic compounds, including oligomers such as DNA, RNA, polypeptides, and other multiunit molecules that have a defined sequences. See, for example, European Patent Application No. 83112493.8 to Steven A. Benner and Genetics Institute. However, magnetic particles have not been suggested as retrievable supports for target capture and background removal.

Other utilization of magnetic particles has included magnetic fluids in the blood. R. Neubauer, *IEEE transactions on magnetics MAG*-9, 445 (1973); attachment of functional group for separation of biomolecules, U.S. Pat. No. 3,970, 518 to I. Giaver; labelling of cell-surface receptors, S. Margel et al., *Jour. Imm. Meth.* 28:341–53 (1979); attachment to drugs for magnetic targeting during therapeutic, A. Senyei et al., *J., App. Phys.*, 49 (6):3578 (1978), K. Wieder et al., *Pro. Soc. of Exp. Bio. Med.*, 58:141 (1978), K. Mosbach and U. Shroeder, *FEBS letters* 102:112 (1979); selective separation of viruses, bacteria, and other cells, R. Molday et al., *Nature* 268:438 (1977); and incorporation of magnetic particles as support in gel affinity chromatography for biological polymers, K. Mosbach and L. Anderson, *Nature* 270:359 (1977), which are incorporated herein by reference.

The use of a two probe system to effect target capture on conventional non-retrievable supports has been suggested in an article authored by Ann-Christine Syuänen, Matti Laaksonen and Hans Söderlund entitled "Fast Quantification of Nucleic Acid Hybrids by Affinity-Based Hybrid Collection;" Nucleic Acids Research, 14(12):5037 (1986).

SUMMARY OF THE INVENTION

It is an object of the present invention to provide methods, reagents, compositions, kits, and instrumentation for performing assays for target molecules of interest. Other objects will be presented hereinafter. For convenience, without limitation embodiments of the present invention can be grouped into areas of target capture, background capture, and combinations thereof.

Turning first to target capture, an embodiment of the present invention feature capture and release cycles to isolate target molecules. The method includes contacting a sample medium potentially containing target molecules with probes and a first support associated or capable of associating with at least one probe under binding conditions. The probes are capable of selectively reversibly binding to the target molecule to form a complex including the probe target and the first retrievable support. Next, the support is separated from the sample medium and brought into contact with a second medium. Next, the support is subjected to releasing conditions to release the target from the support and the support is separated from the second medium. Next, a second support is contacted with the second medium under binding conditions. The second support is associated with or capable of associating with at least one probe capable of selectively binding to the target molecule. Under binding conditions, the target forms a complex with the probe associated to second support for further processing.

Preferably, the first support is retrievable in the sense that it is capable of substantially homogeneous dispersion within the sample medium and can be substantially physically separated, retrieved, or immobilized within the sample medium.

Separation of the first support from the first medium removes nonspecifically bound cellular debris attached to the first support. Further binding of the target molecule to a second support further concentrates the target for detection and permits further release-capture cycles for greater purification.

A further embodiment of the present method features a retrievable support. The method includes contacting the sample potentially carrying target nucleic acid with a retrievable support in association with a probe moiety. The retrievable support is capable of substantially homogenous dispersion within a sample medium. The probe moiety may be associated to the retrievable support, by way of example, by covalent binding of the probe moiety to the retrievable support, by affinity association, hydrogen bonding, or nonspecific association.

The support may take many forms including, by way of example, nitrocellulose reduced to particulate form and retrievable upon passing the sample medium containing the support through a sieve; nitrocellulose or the materials impregnated with magnetic particles or the like, allowing the nitrocellulose to migrate within the sample medium upon the application of a magnetic field; beads or particles which may be filtered or exhibit electromagnetic properties; and polystyrene beads which partition to the surface of an aqueous medium.

A preferred embodiment of the present invention includes a retrievable support comprising magnetic beads characterized in their ability to be substantially homogeneously dispersed in a sample medium. Preferably, the magnetic beads contain primary amine functional groups which facilitate covalent binding or association of a probe entity to the magnetic support particles. Preferably, the magnetic support beads are single domain magnets and are super paramagnetic exhibiting no residual magnetism. The first probe includes a probe ligand moiety capable of specifically binding to antiligand under binding conditions. The retrievable support is capable of substantially homogeneous dispersion within the sample media and includes at least one antiligand moiety capable of binding to ligand under binding conditions to form a target-probe support complex. Next, the retrievable support and sample medium are separated to allow the sample medium to be processed further.

Embodiments of the invention are suitable for capturing target molecules from a clinical sample medium containing extraneous material. The order of contacting the sample medium with probe or retrievable support is a matter of choice. However, the choice may be influenced by the kinetics of binding between the probe and target on one hand, and between the probe ligand and support antiligand on the other.

As applied to polynucleotide target molecules and homopolymer ligands and antiligands, the homopolymer ligand and antiligand binding is generally faster than probe binding to target. Probe binding to the target is sterically impaired after the probe ligand is bound to the support antiligand. A preferred embodiment includes contacting the sample medium with the reagent and bringing the mixture to hybridization conditions. Next, the retrievable support is dispersed in the reagent and sample medium allowing the formation of a target-probe complex in advance of the formation of probe support complexes.

A further embodiment of the present invention features a multiple probe system.

Preferably the method includes a reagent including a first probe as previously described and at least one second probe capable of binding to the target molecule and having label moieties capable of detection. The second probe is capable of forming a target (first and second) probe-support complex. The step of separating the retrievable support from the sample medium not only removes extraneous material from the target-(first and second) probe-support complex, but also separates any second probe which is not bound to the target. Second probe unbound to target contributes to background noises, false signals indicating the presence of target.

Further processing may include release of the target (first and second) probe complex from the retrievable support into a second medium and rebinding of the target (first and second) probe complex to new support. The first retrievable support may carry nonspecifically bound materials which can interfere with assay procedures. Thus, after the release of the target-probe complex from the retrievable support and the retrievable supports removal, a second support having an antiligand moiety capable of binding to the probe ligand can be brought into contact with the target-probe complex under binding conditions to effect a further cycle of target-probe binding or capture for further purification and concentration of target-probe complex.

Further processing may include background capture. A further embodiment of the present invention includes a method wherein the second probe has a second ligand moiety. The method further includes a background support having a second antiligand moiety. The second ligand moiety and second antiligand moiety are capable of stably binding under binding conditions only when the second probe is unbound to the target molecule. The method further includes the step of contacting a medium potentially containing second probe unbound to target with a background support under binding conditions. Next, the background support is separated from the medium to remove unbound second probe reducing background noise.

The term "background support" is used in the conventional sense to include filters and membranes as well as retrievable supports. Binding to the background support does not need to be releasible.

A preferred retrievable support includes, by way of example without limitation, particles, grains, beads, or filaments capable of dispersion within and separation from a medium. Methods of separation include by way of example, without limitation, of filtration, centrifugation, precipitation, surface floatation, settling, or the introduction of electromagnetic fields.

The present method can be applied to polynucleotide target molecules. Preferably, the first and second probes bind quickly to a polynucleotide target "in solution" as opposed to the situation where either the target or probe is immobilized.

The retrievable support, capable of substantial dispersion within a solution, permits interactions between the retrievable support and probes which mimic "in solution" hybridization. In solution, hybridization can be completed in approximately 3–15 minutes. The rapid hybridizations and simplicity of the present methods permit automation. The present method allows nucleic acid sequences contained in clinical samples to be separated from extraneous material allowing the methods to be applied to nonisotopic labeling techniques.

An embodiment of the present method where the target molecule is a polynucleotide, includes contacting a sample medium with reagent under binding conditions. The reagent includes at least one first polynucleotide probe and at least one second polynucleotide probe. The first probe is capable of forming a complex with the target molecule and has a first homopolymer ligand moiety. The second probe is capable of forming a complex with the target molecule in addition to the first probe. The second probe includes a label moiety which has a second homopolymer ligand moiety which is different than the first homopolymer ligand of the first probe. Next, the reagent and sample medium are contacted with a background support and a target capture support. The background support includes at least one second homopolymer antiligand moiety capable of binding to the second homopolymer ligand moiety of the second probe when said second probe is unbound to target. The target capture support includes at least one first homopolymer moiety capable of binding to the first homopolymer ligand moiety of the first probe. The background support and the target capture support remove background noise and the target capture support further concentrates the target-(first and second) probe complex for further processing and separates the target-(first and second) probe complex from cellular debris. Further processing includes the detection of the label moiety indicative of the presence of the target molecule.

Turning now more specifically to embodiments of the invention pertaining to background capture, one embodiment includes a method wherein probe and target are allowed to form a complex. Next, uncomplexed probe is brought into contact with a support under binding conditions. The support is capable of selectively binding unbound probe. Next, the support is separated from the probe-target complex.

A still further embodiment of the present invention includes a method of separating a plurality of target molecules for further processing.

One embodiment includes the sequential addition and removal of probes specific to target molecules on a plurality of supports. A further embodiment includes a method which includes contacting a sample with a first series probe and capturing the target and probe on a plurality of supports. The first series probe includes a ligand capable of association with the support. The first probe series includes probes for all plurality targets which are capable of binding to supports specific for each target molecule. The supports are capable of being separated from each other, the separation of which results in individual types of target molecules being isolated with the support.

A further embodiment of the present invention includes a reagent composition. The reagent composition includes a first probe and a second probe. The first probe is capable of forming a complex with a target molecule and includes a probe ligand moiety capable of specifically binding to antiligand under binding conditions. The second probe is capable of forming a complex with the target molecule and includes a label moiety capable of detection. The reagent composition can be used to capture and detect the target in a sample medium when used with a retrievable support having antiligand moieties.

A further embodiment of the present reagent composition includes a second probe having a second ligand moiety capable of stably binding to an antiligand only in the situation where the second probe is unbound to the target molecule. The reagent composition allows background noise to be reduced by contacting sample potentially containing an unbound second probe with a background support having a second antiligand moiety.

A further embodiment includes a support capable of substantially homogeneous dispersion in a sample medium having oligonucleotide antiligands adapted for binding to oligonucleotide ligands on probes.

A preferred embodiment of the support includes, by way of example, particles, grains, filaments, and beads capable of separation. Means of separation include, by way of example without limitation, precipitation, settling, floatation, filtration, centrifugation, and electromagnetism.

A preferred embodiment includes polystyrene beads, between 10–100 microns in diameter, which are capable of substantially homogeneous dispersion and separation from a medium by filtration or floatation. Another preferred embodiment includes ferromagnetic beads. A ferromagnetic bead marketed under the trademark BIO-MAG is capable of substantially homogeneous dispersion in an aqueous medium and can be retrieved or immobilized by an electromagnetic field. The ferromagnetic bead includes an iron core which is coated with an amine reactive covering. The beads are generally spherical and have a diameter of one micron. The polystyrene and ferromagnetic beads are treated to include antiligand moieties.

A further embodiment of the present invention includes a kit for performing assays for target molecules which are part of a biological binding pair. In the case where the target is a polynucleotide having a specific base sequence, the kit includes a reagent wherein the reagent includes a first polynucleotide probe and a second polynucleotide probe. The first and second probes are capable of binding to mutually exclusive portions of the target to form a complex in which both probes are bound to the target. The first probe is capable of reversibly binding to a first support under binding conditions, and the second probe includes a label moiety capable of detection. The kit further includes a first support allowing the support to form complexes with the target and probes which can be selectively separated from the sample medium.

A further embodiment of the present kit includes a second probe and a background support. The second probe, when not bound to the target, is capable of selectively binding to a background support. The background support capable of being separated from a medium containing reagent to remove the nonspecifically bound second probe.

A further embodiment of the present invention includes an instrument for performing assays in accordance with the present method. In the situation where the target is a polynucleotide, the instrument includes a reaction chamber adapted for receiving reagent and target in a substantially mixed homogeneous state. The reagent includes a first and a second polynucleotide probe. Each probe is capable of binding to mutually exclusive portions of the target forming a complex in which both probes are bound to the target. The first probe is capable of reversibly binding to a first support under binding conditions and the second probe includes a label moiety capable of detection. The instrument further includes means for contacting a first support with the reagent and sample to allow the first probe and target-probe complex to become bound to the support. The instrument further includes means for bringing the sample, reagent, and support to binding conditions to form target-probe complexes bound to support. The instrument further includes means for bringing the first probe into releasing conditions. Finally, the instrument includes means for separating the support from the sample and from the reagent.

The term "reaction vessel" is used in a broad sense to include any means of containment including, by way of example without limitation, cuvettes, test tubes, capillaries, and the like.

Suitable means for bringing the sample, reagent, and support into binding conditions or bringing reagent and support into releasing conditions include by way of example, temperature controls which can elevate or lower the temperature of the sample, reagent, and support to selectively denature or anneal polynucleotide strands.

Suitable means for separating the support from the reagent or sample include by way of example, electromagnets for use in conjunction with magnetic beads, fibers affixed to an anchoring support, centrifuges for use with polystyrene grains, and the like.

Further embodiments of the present invention include means for bringing the reagent and target into contact with background support under binding conditions to remove any second probes having label moieties which second probes are not specifically bound to the target.

Embodiments of the present instrument adapted for use with luminescent label moieties include suitable label excitation means. Instruments for use with fluorescent label moieties include lasers or light emitting assemblies with filters to define appropriate wave lengths. Instruments for use with chemiluminescent label moieties include injection apparatus for injecting cofactors into the reaction chamber.

Turning now to the drawings, which by way of illustration depict preferred embodiments of the present invention, and in particular FIG. 1, a method of procedure, with necessary reagent compositions, is illustrated in schematic form for an assay for target polynucleotide strands. Conventional assay techniques include many target strands, and many probe strands would be used to perform an assay. However, for the simplicity to further an understanding of the invention, the illustration depicts only limited numbers of probes, support entities, and targets. FIG. 1 features a method utilizing retrievable supports.

Step 1 of the assay illustrated in FIG. 1 begins with a clinical sample which, by way of illustration, contains cells. The cells potentially carry target nucleic acid, either DNA or RNA, having a base sequence of particular interest indicative of pathogens, genetic conditions, or desirable gene characteristics. The clinical samples can be obtained from any excreta or physiological fluid, such as stool, urine, sputum, pus, serum, plasma, ocular lens fluid, spinal fluid, lymph, genital washings, or the like. Individuals skilled in the art may desire to reduce biopsy samples to single cell suspensions or small clumps by means known in the art. For example, biopsy samples of solid tissues can be effectively reduced to single cell suspensions or to small clumps of cells by agitating the biopsy sample in a mixture of 0.5M sodium chloride, 10 mM magnesium chloride, 0.14M phosphate buffer, pH 6.8, and 25 Mg/ml cyclohexamide. Isolation of specific cell types by established procedures known in the art, such as differential centrifugation, density gradient centrifugation, or other methods, can also be applied at this step.

The cells are then treated to liberate their DNA and/or RNA. Chemical lysing is well known in the art. Chemical lysing can be performed with the dilute aqueous alkali, for example, 0.1 to 1.0M sodium hydroxide. The alkali also serves to denature the DNA or RNA. Other denaturization and lysing agents include elevated temperatures, organic reagents, for example, alcohols, amides, amines, ureas, phenols and sulfoxides, or certain inorganic ions, for example chaotropic salts such as sodium trifluoroacetate, sodium trichloroacetate, sodium perchlorate, guanidinium isothiocyanate, sodium iodide, potassium iodide, sodium isothiocyanate, and potassium isothiocyanate.

The clinical sample may also be subjected to various restriction endonucleases to divide DNA or RNA into discrete segments which may be easier to handle. At the completion of the sample processing steps, the clinical sample includes sample nucleic acid, cellular debris, and impurities. In the past, sample nucleic acid was separated from cellular debris and impurities by nonspecific binding of the nucleic acid to filters or membranes and washing cellular debris and impurities from the filter or membrane. However, in practice, some cellular debris and some impurities, as well as nontarget nucleic acid, are nonspecifically bound to the filter or membrane and are not removed by washes.

An embodiment of the present invention, as illustrated in Step 1, includes contacting the sample potentially carrying target nucleic acid with a retrievable support in association with a probe moiety. The retrievable support is capable of substantially homogenous dispersion within a sample medium. The probe moiety may be associated to the retrievable support, by way of example, by covalent binding of the probe moiety to the retrievable support, by affinity association, hydrogen binding, or nonspecific association.

The support may take many forms including, by way of example, nitrocellulose reduced to particulate form and retrievable upon passing the sample medium containing the support through a sieve; nitrocellulose or the materials impregnated with magnetic particles or the like, allowing the nitrocellulose to migrate within the sample medium upon the application of a magnetic field; beads or particles which may be filtered or exhibit electromagnetic properties; and polystyrene beads which partition to the surface of an aqueous medium.

A preferred embodiment of the present invention includes a retrievable support comprising magnetic beads characterized in their ability to be substantially homogeneously dispersed in a sample medium. Preferably, the magnetic beads contain primary amine functional groups which facilitate covalent binding or association of a probe entity to the magnetic support particles. Preferably, the magnetic support beads are single domain magnets and are super paramagnetic exhibiting no residual magnetism.

The particles or beads may be comprised of magnetite particles, although they can also be other magnetic metal or metal oxides, whether in impure, alloy, or composite form, as long as they have a reactive surface and exhibit an ability to react to a magnetic field. Other materials that may be used individually or in combination with iron include, but are not limited to, cobalt, nickel, and silicon. Methods of making magnetite or metal oxide particles are disclosed in Vandenberghe et al., "Preparation and Magnetic Properties of Ultrafine Cobalt Ferrites," *J. of Magnetism and Magnetic Materials*, 15 through 18:1117–18 (1980); E. Matijevic, "Mono Dispersed Metal (Hydrous) Oxide—A Fascinating Field of Colloidal Science," *Acc. Chem. Res.*, 14:22–29 (1981), the disclosures which are incorporated herein by reference.

A magnetic bead suitable for the present invention includes a magnetic bead containing primary amine functional groups marketed under the trade name BIO-MAG by Advanced Magnetics, Inc. A preferred magnetic particle is nonporous yet still permits association with a probe moiety. Reactive sites not involved in the association of a probe moiety are preferably blocked to prevent nonspecific binding of other reagents, impurities, and cellular material. The magnetic particles preferably exist as substantially colloidal suspensions. Reagents and substrates and probe moieties associated to the surface of the particle extend directly into the solution surrounding the particle. Probe moieties react with dissolved reagents and substrates in solution with rates and yields characteristic of reactions in solution rather than rates associated with solid supported reactions. Further, with decreasing particle size the ratio of surface area to volume of the particles increases thereby permitting more functional groups and probes to be attached per unit weight of magnetic particles.

Beads having reactive amine functional groups can be reacted with polynucleotides to covalently affix the polynucleotide to the bead. The beads are reacted with 10 percent glutaraldehyde in sodium phosphate buffer and subsequently reacted in a phosphate buffer with ethylenediamine adduct of the phosphorylated polynucleotide in a process which will be set forth in greater detail in the experimental protocol which follows.

Returning now to Step 2, the retrievable support with associated probe moieties is brought into contact with the clinical sample and, progressing through to Step 3, is brought into binding conditions. The probe moiety specific for the target of interest becomes bonded to the target strands present in the clinical sample. The retrievable support, dispersed throughout the sample and reagent medium, allows the probe moieties and target to hybridize as though they are free in a solution.

Hybridizations of probe to target can be accomplished in approximately 15 minutes. In contrast, hybridizations in which either the probe or target are immobilized on a support not having the capability to be dispersed in the medium may take as long as 3 to 48 hours.

Extraneous DNA, RNA, cellular debris, and impurities are not specifically bound to the support. However, as a practical manner, a small amount of extraneous DNA, RNA, cellular debris, and impurities are able to and do in fact nonspecifically bind to any entity placed within the reaction vessel including the retrievable support. Embodiments of the present invention facilitate the further purification of clinical samples to remove extraneous DNA, RNA, cellular debris, and further impurities from target polynucleotides.

Step 4 of FIG. 1 depicts the separation of the support of the clinical sample and the suspension of the support into a second medium. The second medium thus includes the retrievable support with the associated probe bound to target polynucleotide strands. Also carried with the retrievable support is extraneous DNA, RNA, cellular debris, and impurities nonspecifically bound to the support, but in a much lower concentration than what was initially found in the clinical sample. Those skilled in the art will recognize that some undesirable materials can be reduced by washing the support prior to suspension in the second medium.

The retrievable support with associated probe and target strands suspended in the second medium is subject to further denaturation as set forth in Step 5 thereby allowing the target to disassociate from the probe moieties of the retrievable support. The denaturation process may or may not release nonspecifically bound extraneous DNA, RNA, cellular debris, or impurities from the retrievable support. However, Step 5 of the present method allows the retrievable support to be removed from the second medium carrying with it much of the nonspecifically bound cellular debris, impurities, and extraneous DNA, and RNA initially carried over from the first clinical sample medium.

As set forth in Step 6, a new support can be introduced into the second medium under binding conditions to again capture target polynucleotide strands on probe moieties associated with the retrievable support. It will be recognized by those skilled in the art that the new support may actually include the original retrievable support after recycling steps to further purify and remove nonspecifically bound DNA, RNA, cellular debris, and impurities. Thus, the only impurities present in the second medium include DNA, RNA, cellular debris, and impurities previously nonspecifically bound to the support which has subsequently been released from the first support and dissolved or suspended in the second medium.

However, such impurities can be further removed from the target polynucleotides by removing the second retrievable support from the second medium and again repeating the cycle of introducing the retrievable support into a further medium, denaturation, and removal of the old support. Those skilled in the art will recognize that the magnetic beads described in the present invention are susceptible of being raised out of a solution or being held in place as a solution is removed or added to a containment vessel.

The ability of the magnetic beads to participate in the reactions which mimic "insolution kinetics" strands allow the completion of a cycle of denaturation and binding to the target to be accomplished in three to fifteen minutes.

After sufficient purification and concentration, the target can be detected by luminescent or radioactive methods known in the art as indicated in Step 8. Purification of the medium containing the target allows the detection of nonisotopic label moieties without cellular debris and impurities.

Turning now to FIG. 2, which features a multiple probe method, a further embodiment to the present assay method is illustrated beginning with a clinical sample containing polynucleotide target which is processed in accordance with the clinical sample of the previous figure with the introduction of solubilizing agents and reagent. The reagent of the assay method depicted in FIG. 2 includes a first polynucleotide probe strand ($P_1$) and a second polynucleotide probe strand ($P_2$) capable of forming a complex with the target in which both probes ($P_1$ and $P_2$) are bound to the target. The first probe ($P_1$) is capable of associating with a retrievable support ($S_1$) under binding conditions. The second probe has at least one label moiety capable of detection. The label moiety is illustrated in the drawings with an asterisk or a star. Following the introduction of solubilizing agents and reagent under denaturation conditions, the solution containing the clinical sample potentially includes target polynucleotides and reagent in the form of the first and second probes, plus cellular debris, solubilizing agents, impurities, and extraneous RNA and DNA.

Under binding conditions as illustrated in Step 2, the first and second probes ($P_1$ and $P_2$) bind to mutually exclusive portions of the target. The hybridization of the probes ($P_1$ and $P_2$) to the target in solution is rapid and unimpaired by association with a solid support. In order to insure the binding of the target to the first and second probe strands ($P_1$ and $P_2$) an excess of probe is employed. However, even if an excess of probe ($P_1$ and $P_2$) were not employed, some probe would fail to find target and would remain unhybridized in the sample medium. The unhybridized second probe ($P_2$) having a label moiety constitutes background noise if present during detection.

The first probe ($P_1$) is capable of binding to a support ($S_1$) by means of a ligand capable of binding to an antiligand moiety on a support. The ligand ($L_1$) includes, by way of example, a tail portion comprising a homopolymer. The support ($S_1$) includes an antiligand ($A_1$) capable of receiving and binding to ligand ($L_1$). The antiligand ($A_1$) includes, by way of example, a homopolymer complementary to the ligand ($L_1$) of probe ($P_1$).

Turning now to Step 3, under binding conditions the antiligand moiety ($A_1$) of support ($S_1$) associates or binds to the ligand moiety ($L_1$) of the first probe ($P_1$) which is itself bound to the target and linked to the second probe ($P_2$). The support may take many forms. Beads or particulate supports can be dispersed in solution and participate in binding with target probe reactions which demonstrate near in solution kinetics. Further, retrievable beads and particulate supports can separate probe-target complexes from nondissolvable debris without clogging problem inherent in more conventional filters or membranes.

However, conventional membranes, filters, or cellulose supports may also be employed for some applications in which clogging may not be a problem. Due to the rapid hybridization of the probes to target insolution, a solid nonbead or nonparticulate membrane or filter support can be incorporated into the reaction vessel. The solution of reagent and sample can be passed through the support to affect target capture. The support ($S_1$) is illustrated in FIG. 2 as a retrievable support.

In solution with the target-probe support complex are unbound first and second probe moieties, unbound target solubilizing agents, impurities, and cellular debris. The unbound second probe ($P_2$) which has label moieties constitutes noise, producing a signal which mimics the presence of target. A small amount of extraneous cellular debris, solubilizing agents, impurities, and probes may also become nonspecifically bound to the retrievable support.

In Step 4, the support ($S_1$) is separated from the clinical sample medium. If a retrievable support is used, separation can be accomplished either by immobilizing the retrievable support within a reaction vessel or by withdrawing the retrievable support from the sample medium directly. Those skilled in the art will recognize that the immobilized support can be washed to reduce undesirable material.

Turning now to Step 5, the target-probe support complex is substantially free of extraneous RNA, DNA, solubilizing agents, impurities, and cellular material and can be monitored for the presence of the label moieties indicative of the presence of the target molecule. However, a small amount of extraneous DNA, RNA, solubilizing agents, impurities, and cellular materials may still be nonspecifically bound to the support ($S_1$). Moreover, unbound, in the sense that it is not associated with target, second probe ($P_2$) may also be nonspecifically bound to the support ($S_1$) and can affect signals from nonisotopic label moieties. The presence of unbound second probe moiety ($P_2$) having label moieties is a significant cause of background noise thereby reducing the accuracy of the assay procedure.

Thus, as an alternative Step 5, the first support ($S_1$) may be suspended into a second medium where the support ($S_1$) is separated from the target-probe complex by denaturation.

Following denaturation, in Step 6, the first support ($S_1$) is removed from the second medium and replaced with a second support ($S_2$). The second support ($S_2$) includes an antiligand moiety ($A_1$) capable of binding to the ligand moiety ($L_1$) of the first probe.

Moving to Step 7, under binding conditions, the target-probe complex reassociates with the second support ($S_2$). The removal of the first support ($S_1$) removes extraneous material, debris, and probes nonspecifically bound to the first support ($S_1$) from the assay medium.

As illustrated in Step 8, the medium containing the target-probe complex can be monitored for the presence of the labels. However, further purification of the assay medium can be performed to further reduce the presence of background and extraneous materials which may have been carried from the sample medium nonspecifically bound to the first retrievable support ($S_1$) and subsequently dissolved or disassociated from the first support ($S_1$) into the second medium.

Thus, the second retrievable support ($S_2$) may be brought into contact with a third medium, the medium brought into conditions to release the target-probe complex from the support, and the support removed to complete a further cycle. The number of cycles will be a matter of choice depending on the type of sample, type of label moieties, and the sensitivity of the detection equipment. Different types of supports may be used at different times. Thus, a retrievable support can be used to gather or concentrate the target-probe complexes from sample mediums or solutions initially to avoid problems of clogging typical of membranes or filters. The second or third supports preferably includes a membrane or filter with antiligand moieties ($A_1$) which bind to the ligand moiety ($L_1$) of the first probe ($P_1$). Membrane or filter supports can simplify process steps allowing flow-through recovery of target-probe complexes.

A further embodiment of the present invention is particularly well suited for reducing background noise. Referring now to FIG. 3, a modification of the previous assay procedure illustrated in FIG. 2 is described. In FIG. 3, a target polynucleotide has formed a complex with a first and second probe moiety (P1 and $P_2$) similar to the probe moieties described in FIG. 2. However, the second probe includes a second ligand ($L_2$). The second ligand ($L_2$) may include, by way of example, a single terminal ribonucleotide which complexes with a borate antiligand, an alternating copolymer which binds with a complementary copolymer, a biotin ligand which binds to an avidin antiligand, or as illustrated, homopolymer ligand ($L_2$), and a complementary homopolymer antiligand ($A_2$).

Turning now to Step 1, a background support capable of selectively binding to the second probe ($P_2$) only when it is not bound to a target, is brought into contact with the medium containing the target-probe complex. The medium further includes free, disassociated first and second probes ($P_2$ and $P_2$). The labeled second probe ($P_2$), which contributes to the background noise, is specifically bound to the background support ($B_1$) by a vast molar excess of antiligand moieties ($A_2$) associated with the background support ($B_1$). Following binding of the unbound labeled probe ($P_2$) to the background support ($B_1$), the background support ($B_1$) is removed from the medium as illustrated in Step 2. The medium containing the target-probe complex can be monitored for the presence of the label contained upon the second probe ($P_2$) with a reduction in background noise. Alternatively, the medium containing the target-probe complex can be subjected to further processing.

The further processing can include further background reduction by repeating Steps 1 through 3 described in FIG. 3 or, steps previously described in conjunction with FIG. 2. For example, background reduction steps can be incorporated into the processing of a clinical sample as illustrated in FIG. 2 at any point in which the ligand and antiligand moieties of the first and second probes do not interfere, and the target is complexed with the first and second probes.

Figure 4:
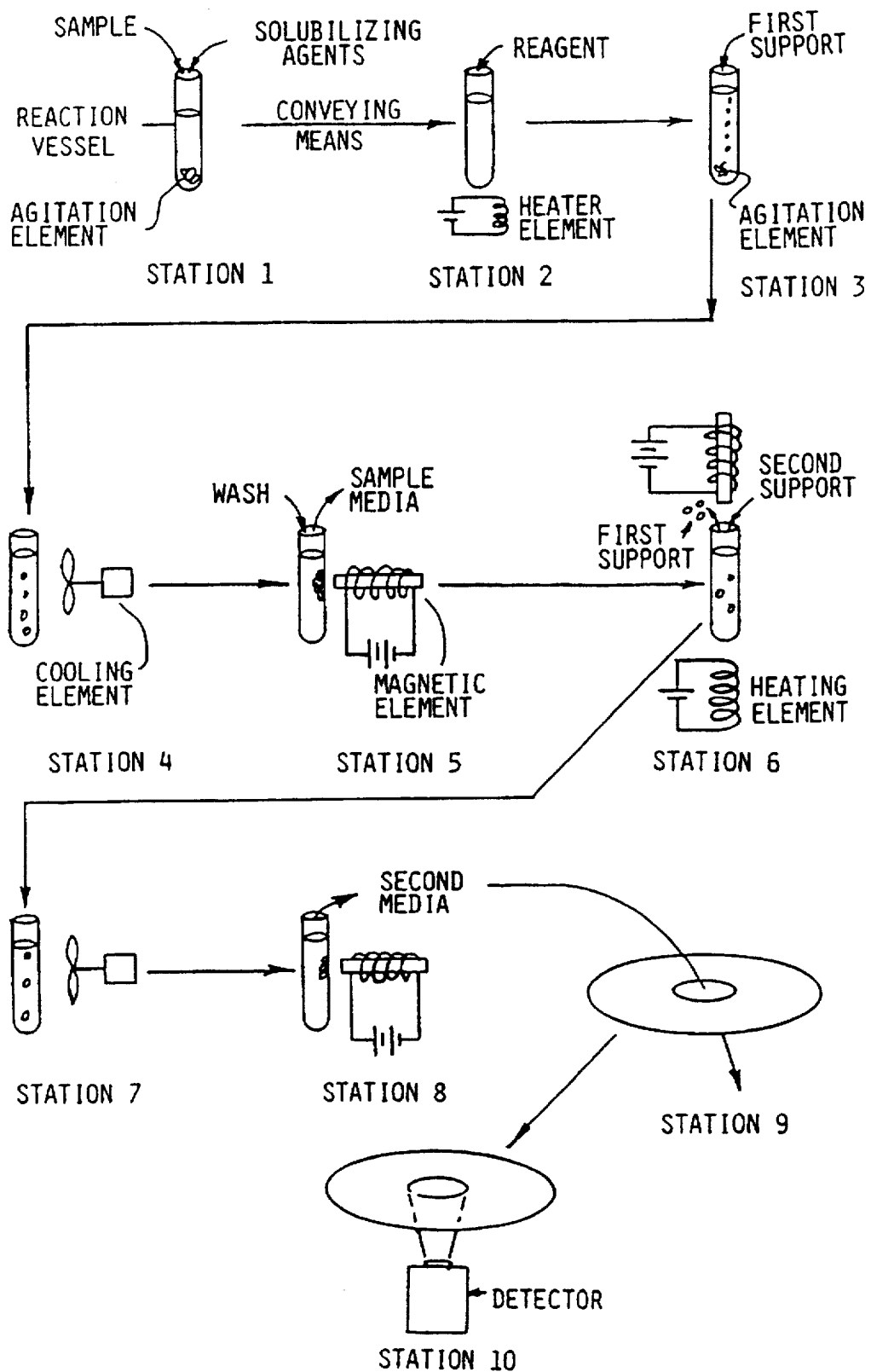

An embodiment of present methods may be practiced with an aid of apparatus set forth in schematic form in FIG. 4. The apparatus includes the following major elements: at least one containment vessel, means for controlling the association of a probe with a target molecule and a retrievable support, means for separating the retrievable support from a sample solution, and means for releasing the target molecule from the retrievable support. These major elements may take various forms and are described more fully below.

The apparatus will be described below for illustration purposes as applying the methods described in FIGS. 2 and 3 relative to a target molecule which includes a polynucleotide. Thus, at Station 1, a clinical sample is placed within the containment vessel with solubilizing agents such as chaotropic salts, enzymes, and surfactants in order to dissolve cellular material and release nucleic acids. The containment vessel may include agitation elements to facilitate the break up of cells. The containment vessel may include any type of vessel, tube, cuvette suitable for containing the sample.

In an instrument designed for automated analysis, the apparatus set forth in FIG. 4 will preferably include means for receiving a plurality of containment vessels. For illustration purposes, the containment vessels containing the sample are analyzed sequentially. Thus, containment vessels are conveyed to a first station and then to subsequent stations where various steps of the assay method are performed.

The various stations are linked by conveying means. Conveying means may include a rotatable turntable, conveying belt, or the like. As applied in a clinical hospital setting, conveying means may include manual movement. Thus, hospital staff may obtain a tissue sample from a patient and place the sample in the containment vessel. Sample processing, including the breakup of the tissue sample and initial mixing of solubilizing agents and reagents would be initiated at bedside and continued as the containment vessel traveled to a subsequent station for further processing. References to stations are for illustration purposes. Those skilled in the art will recognize that certain stations or steps may be combined or reversed.

Returning now to the first station, sample and solubilizing agents are placed within a containment vessel in which an agitation element thoroughly mixes the sample and solubilizing agents, releasing nucleic acids from cellular materials. Conveying means carry the containment vessel to Station 2 where the containment vessel receives reagent.

The reagent includes a first polynucleotide probe and a second polynucleotide probe. The first and second probes are capable of forming a complex with the target polynucleotides in which both probes are bound to mutually exclusive portions of the target. The first probe is also capable of binding to a retrievable support under binding conditions. The second polynucleotide probe includes a label moiety capable of detection. The reagent and sample nucleic acid are denatured by a heating element and conveyed to Station 3.

At Station 3, the containment vessel receives a first support depicted by open circles. The first support is homogeneously dispersed within the sample medium by suitable means including an agitation element. Examples of suitable supports include, without limitation, polystyrene beads, magnetic beads and other particulate or filamentous substances. As illustrated, the first support includes a magnetic bead having polynucleotide antiligands of deoxythymidine (dT). The first probe includes a tail portion of deoxyadenosine (dA) capable of binding to the first support during binding or hybridization conditions.

Moving to Station 4 hybridization conditions are imposed upon the sample medium by cooling by a cooling element. However, those skilled in the art will recognize that means to alter salt concentrations can be readily substituted for thermal controls. Thus, the target polynucleotide forms a complex with the first and second probes. Further, the homopolymer deoxyadenosine (dA) tail portion of the first probe hybridizes to the deoxythymidine (dT) homopolymer of the retrievable support.

From Station 4, the containment vessel is moved to Station 5 where the retrievable support is immobilized on the wall of the containment vessel by activating a magnetic element. If polystyrene beads were substituted for magnetic bands, the polystyrene bead would be immobilized by filtering or density differences. The sample medium is disposed of carrying with it most of the extraneous DNA, RNA, solubilizing agents, cellular material, and impurities. The immobilized retrievable support is washed to further remove extraneous DNA, RNA, solubilizing agents, cellular materials, and impurities.

Further, although it is illustrated that the retrievable support is immobilized on the wall of the reaction vessel, it is also possible to remove the retrievable support from the reaction vessel by a magnetic element and dispose of the first reaction vessel containing with it extraneous DNA, RNA, solubilizing agents, and cellular material which may be nonspecifically bound to the reaction vessel walls.

The retrievable support is placed in a second medium, either the same containment vessel or a new containment vessel. The containment vessel, containing the retrievable support in a second medium is carried to Station 6.

At Station 6, the second medium is brought to denaturization conditions by suitable means including a heating element. The denaturization process releases the target-first and second-probe complex from the (dT) homopolymer of the retrievable support. The first support, potentially carrying extraneous DNA, RNA, impurities, and cellular material, is removed from the second medium. A background support is then brought into contact with the second medium and passed to Station 7.

At Station 7 a cooling element brings the second medium to hybridization temperatures. The background support includes a second antiligand capable of specifically binding to a ligand carried upon the second probe. For example, without limitation, a terminal nucleotide of the second probe can be synthesized to be a ribo derivative which specifically binds to borate moiety carried upon the second support. The second probe bound to the target as part of a probe target complex will not bind to the borate carried upon the third support due to stearic hindrances. However, unbound second probe will specifically bind to the borate support. Alternatively, the second probe may include a homopolymer such as deoxycytosine (dC) which binds to a deoxyguanine (dG) homopolymer linker on a second support. The length of the homopolymers are designed such that complexes of the target-first and second probes with the second support are not stable; however, complexes of the second probe alone with the second support are stable within reaction parameters. Indeed, background capture binding of background support to unbound second probe can be irreversible.

Next, the containment vessel containing the second medium and the background support is conveyed to Station 8 where the background support having second probe strands unbound to the target-probe complex is separated from the second medium. Separation of the background support removes nonspecific background noise from the medium.

As illustrated, background capture is effected upon beads. However, those skilled in the art will recognize that the initial purification of the target-first and second probe complex from the clinical sample, removes all or most solid debris allowing background capture on filter or membrane supports through which the second medium can be flushed.

From Station 8 the purified medium containing the target-probe complex with reduced background is conveyed to Station 9. At Station 9, a third support, depicted as a membrane or filter, is brought into contact with the second medium which is brought to hybridization temperatures by a heating element. The third support includes first antiligand moieties which bind to the first ligand moieties of the first probe. Thus, if the first ligand moiety of the first probe is of a homopolymer of deoxyadenosine (dA), the third support may include homopolymer of deoxythymidine (dT). As illustrated, the third support includes filters or membranes through which the second medium can be flushed; however, beads or particles may also be used. The third support serves to further concentrate the target-first and second probe complex and permits further reduction of background and interfering materials which do not specifically bind to the third support. Moving to Station 10, the third support concentrates the target-first and second probe complex allowing detection of label moieties carried upon the second probe.

The present invention is further described in the following typical procedures and experimental examples which exemplify features of the preferred embodiment.

I. Procedures

A. Materials

All reagents were of analytical grade or better. Magnetic beads marketed under the trademark BIO-MAG containing functional amino groups were obtained from Advanced Magnetics, Inc. of Cambridge, Mass.

In the present example, all labeled nucleotides were obtained from New England Nuclear. The enzyme terminal deoxynucleotidyl transferase (TDT) was obtained from Life Sciences, Inc., St. Petersburg, Fl. The oligonucleotide pdT$_{10}$ was obtained from Pharmacia PL Biochemicals.

B. Synthesis of Probes

Figure 5:
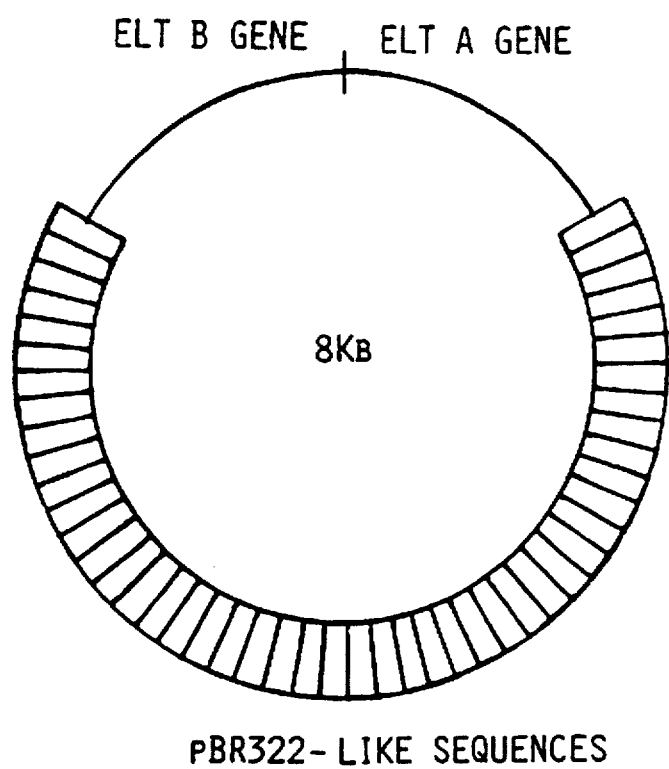

The following sets forth typical protocols and methods. Referring now to FIG. 5, two probes were constructed to the sense strand of the enterotoxin gene elt AI of *Escherichia coli*, in accordance with the constructional map, FIG. 6, of Spicer, E. K. and J. A. Noble, 1982, *J. of Biological Chem.* 257, 55716–55751.

One set of probes was synthesized beginning at position 483 of the gene sequence and extending onward 30 nucleotides in length, hereinafter referred to as the A483 probe. A second probe was synthesized beginning at position 532 in the gene sequence and extending 30 nucleotides in length, hereinafter referred to as the A532 probe. A third probe was synthesized beginning at position 726 in the gone sequence and extending 39 nucleotides in length, hereinafter referred to as the A726 probe. The specific base sequences (5' to 3') are set forth in Table 1 below:

ciation with a support at 37° C., particularly if the probe is bound to target due to steric hindrance and the size of the target-probe complex. Probe A726 was modified by the random addition of approximately three residues of $^{32}$P-dC and $^{32}$P-dG to its 3' end with terminal transferase.

Those skilled in the art will recognize that other probes can be readily synthesized to other target molecules.

C. Preparation

The target in Example Nos. 1, 2 and 3 is the enterotoxin gene elt AI. The enterotoxin gene elt AI is carried as part of the plasmid EWD-299 obtained from Stanford University.

In Example No. 1, enterotoxigenic bacteria were grown to log-phase in Luria broth. The enterotoxigenic bacteria were lysed and the plasmid EWD-299 isolated.

The plasmid EWD-299 was further digested with the restriction enzymes Xba 1 and HIND III. A fragment of 475 base length was used as a target and purified by electro-elution from a 1 percent agarose gel. In order to follow the efficiency of capture steps, the fragment was 5' end labeled with $^{32}$P-ATP with the enzyme polynucleotide kinase following manufacturer's instructions.

In Example Nos. 2 and 3, the enterotoxigenic bacteria and wild type nonenterotoxigenic *E. coli* JM83 were separately grown to log phase. The wild type *E. coli* serves as a control. Separate extracts of enterotoxigenic bacteria and wild type bacteria were prepared by substantially solubilizing the cells in chaotropic solutions. Thus, the bacteria cultures, in Luria broth, were added to solid guanidinium thiocyanate (GuSCN) to a concentration of 5M GUSCN, Tris-HCl to a concentration of 0.3M, and EDTA (pH 7) to a concentration of 0.1M. The chaotropic-bacterial solutions were then heated to 100° C. for five minutes and cooled. The resultant enterotoxigenic bacteria extract was serially diluted with wild type nonenterotoxigenic bacteria extract. The concentration of tox plasmids per cell and the cell number in the extracts were measured by conventional techniques. The original extracts solubilized in GuSCN contained approximately 10$^9$ enterotoxigenic *E. coli* per ml and 100 plasmids/cell.

D. Synthesis of Beads

Retrievable supports were prepared from magnetic beads. Other retrievable supports include particles, fibers, polystyrene beads or other items capable of physical separation from a medium. Magnetic beads were synthesized with an adduct of deoxythymidine of ten base length to allow the beads to associate with probes tailed with deoxyadenosine in a readily reversible manner.

Thus, 100 ml of beads having amine functional groups such as BIO-MAG (M4100) beads were washed four times

TABLE I

| Probe | Sequence |
|---|---|
| A483 | AGA CCG GTA TTA CAG AAA TCT GAA TAT AGC |
| A532 | AGA TTA GCA GGT TTC CCA CCG GAT CAC CAA |
| A726 | GTC AGA GGT TGA CAT ATA TAA CAG AAT TCG GGG GGG GGG |

The probes were synthesized by methods available in the art. The numbering system is adapted from the 768 nucleotide sequence available through Intelligenetics sequence bank ECO ELT AI.

Of the ten G residues at the 3 prime end of probe A726, three guanine bases towards the 5' end are capable of binding to three complementary cytosine bases of the tox gene. Stretches of three cytosines are common in DNA. The ten guanine bases form a ligand capable of binding to a poly C antiligand carried upon a support such as oligo dC-cellulose. However, seven guanine bases will not form a stable assowith 20 mM sodium phosphate (pH 6.7) in four 275 ml T-flasks. The beads were then washed with 1% glutaraldehyde in 20mM sodium phosphate. Next, the beads were reacted in 100 ml of 10 percent glutaraldehyde in 20 mM sodium phosphate (pH 6.7) for three hours at room temperature. The beads were then washed extensively with 20 mM sodium phosphate (pH 6.7) and then washed once with 20 mM phosphate (pH 7.6).

Separately, a purified ethylene diamine (EDA) adduct of pdT$_{10}$ (EDA-dT$_{10}$) was prepared in accordance with Chu, B. C. F., G. M. Wahl, and L. E. Orgel; Nucleic Acid Res. 11, 6513–6529 (1983) incorporated by reference herein. The concentration of EDA-dT$_{10}$ was adjusted to 1 OD/ml in 20 mM phosphate (pH 7.6).

The EDA-dT$_{10}$ was combined with the magnetic beads to allow the EDA-dT$_{10}$ to react with the free aldehyde groups of the beads. The mixture of EDA-dT$_{10}$ and beads was divided into a plurality of 50 ml polypropylene tubes. The tubes containing the reaction mixture and beads were placed in a tube rotator and agitated overnight at room temperature.

Next, the beads were washed five times to remove non-covalently bound EDA-dT$_{10}$ with a wash solution of sterile 20 mM phosphate (pH 6.7) in large 275 ml T-flasks and diluted to 200 ml with the wash solution.

For storage, beads can be maintained for months in a buffer of 20 mN phosphate, to which is added sodium azide to 0.1% and SDS to 0.1%. Bead preparations are stored at 4° C. protected from light.

The beads were then prehybridized to block nonspecific binding sites in a buffer, hereafter referred to as "prehybridization buffer", of 0.75M sodium phosphate (pH 6.8), 0.5% sodium lauroyl sarcosine, 1 Q micrograms/ml $E. coli$ DNA, 0.5 milligram per milliliter mg/ml bovine serum albumin (BSA) (Nuclease-free) and 5 mM ethylenediaminetetraacetic acid) (EDTA). Before applying the probes and beads to target capture procedures, two prehybridizations of the beads were performed. The prehybridization procedure included placing the beads in ten volumes prehybridization buffer.

The first prehybridization procedure was performed with agitation at 60° C. The second prehybridization procedure was performed at room temperature with swirling. A 0.1 percent isoamyl alcohol solution was added to the solutions as a defoamant.

The binding capacity of dT$_{10}$-derivized beads was measured by the following procedure. In separate vessels, dT$_{50}$ and dA$_{50}$ were 5' end labeled with $^{32}$P-dT and $^{32}$P-dA respectively to a specific activity (Sa) of about $10^6$ dpm/microgram. Next, the Sa was accurately measured for a known quantity of reacted dT$_{50}$ by trichloroacetic acid precipitation.

Next, 5 μg of $^{32}$P-dA and 5 μg of $^{32}$P-dT$_{50}$, having substantially identical Sas of between 100,000–200,000 dpm/mg, were separately added to tubes containing prehybridization buffer and brought to a volume of 1 ml.

A known sample volume of prehybridized beads was placed into four tubes. Two of the four tubes each receive 0.5 ml of the $^{32}$P-dA mixture and the remaining two tubes receive 0.5 ml of the $^{32}$P-dT$_{50}$ mixture. All four solutions are brought to hybridization conditions for five minutes. The beads are thereafter immobilized and washed. The activities of the solutions are then monitored. The total binding capacity, C, for a quantity of bead preparation measured in micrograms is set forth below:

$$C = V(A-T)/X$$

In the above equation X is the specific activity of $^{32}$P-dT$_{50}$ in cpm/mg, V is the volume ratio of total volume to sample volume, A is the average activity of the beads suspended in $^{32}$P-dA solutions in cpm, and T is the average activity of the beads suspended in $^{32}$P-dT solutions in cpm.

Those skilled in the art will recognize that other beads, particles, filaments, and the like can be formulated with other nucleotide combinations or homopolymers. For example, polyA-derivized beads were produced by substituting (for the purified EDA adduct of dT$_{10}$) a solution containing 100 mg poly A (mw>100.000) in 50 ml of 20 mM sodium phosphate (pH 7.6).

E. Target Capture Procedures

Bead preparations were used to capture target polynucleotides. The following sets forth a typical experimental target capture protocol demonstrating retrievable supports and reversible captures for purposes of illustration, without limitation, the procedure will be discussed using a first probe A483 and a second probe A532. The first probe, A483, was randomly 3' end labeled with $^{32}$P-dCTP and $^{32}$P-dGTP to a specific radioactivity of about $10^{10}$ dpm/mg. The second probe, A532, was tailed with about 70 unlabeled dA residues by the enzyme terminal transferase.

First, 200 μg/ml of labeled phrobe A483 an 400 μg/ml of tailed probe A532 were mixed with varying amounts of a heat-denatured 475 mer Xba 1-HIND III restriction fragment of the enterotoxin gene at 65° C. for 15 minutes in 1.4M sodium chloride.

Next, target capture was initiated by contacting the medium containing the target and probe moieties with an aliquot of dT$_{10}$-magnetic beads having 3 micrograms/ml of dA$_{50}$ binding capacity following prehybridization procedures to reduce nonspecific binding to the magnetic bead. The magnetic bead and the probe-target complex was incubated at room temperature in 0.1 ml prehybridization buffer in 5 ml polypropylene tubes for two to five minutes.

The tubes were placed into a Corning tube magnetic separator. The Corning tube magnetic separator upon activation imposes a magnetic field through the polypropylene tubes which immobilizes the magnetic beads on the inner walls of the tubes. During the time that the magnetic beads are immobilized on the side walls of the polypropylene tubes, the original medium was removed and discarded.

While immobilized, the beads were washed three times with 0.6 ml of prehybridization buffer containing isoamyl alcohol as a defoamant. Following the addition of the prehybridization buffer, the beads were resuspended by removing the tubes from the magnetic field and by subjecting the medium to vigorous vortexing.

Next, the magnetic field was reapplied to immobilize the beads allowing the prehybridization buffer to be removed and discarded. The cycle of adding the prehybridization buffer, resuspending the beads, immobilizing the beads, and discarding the prehybridization buffer was repeated twice. Target-probe complexes held on the beads are available for further processing including additional steps of detection, background capture or further cycles of target capture.

A preferred target capture procedure includes release of the target-probe complex and recapture on a second support. Preferably the support is chemically distinct from the first support.

Release of the target-probe complex is effected in the following typical protocol. After the removal of the last prehybridization buffer, prehybridization buffer was added to the tube containing the beads. The beads were incubated with agitation at 60° C. for one-two minutes to release the probe-target complexes from the bead. The magnetic separator was again activated with the temperature at 60° C. and the eluate, containing free target-probe complexes, is removed from the tube. The eluate can be recaptured on additional retrievable supports or subjected to final capture on conventional supports. It will be recognized by those skilled in the art that the capture and release of the target probe complex from retrievable supports such as the magnetic beads of the present example can be repeated as often as desired to reduce hybridization backgrounds.

Final capture of the probe-target complex was typically performed on nitrocellulose filters or nylon membranes containing nonspecifically bound or covalently bound dT-3000. Thus, the target-probe complexes carried upon the magnetic beads were released from the magnetic beads by heating the beads to 60° C. in prehybridization buffer for two minutes. The beads were immobilized and the eluate removed and passed through a 0.2 micron acrodisc (Gelman) to remove magnetic fines. The nitrocellulose filter containing dT-3000 selected, bound, and captured the dA tail on the unlabeled probes.

The use of a chemically different solid support for the final capture of the target-probe complex avoids binding background molecules which may have a high affinity for previously used supports. By way of illustration, it is possible for lower level contaminants with a natural high affinity for a particular support to repeatedly bind and elute with a support along with probe-target complexes. Such low level contaminants cannot be diluted out by repeated use of a retrievable support of the same composition as completely as by exposing them to supports of very different compositions. Low level contaminants can also be lowered by utilizing chemically distinct means to release the target-probe complexes from supports and recapture.

F. Background Capture Procedures

Background capture procedures permit the selective reduction of background noise permitting the detection of true signal indicative of the presence of target. Background capture can be applied in a single probe system or in systems using more than two probes. For example, in background capture procedures featuring a single probe, the probe includes a label moiety and a ligand. The probe is capable of binding to a target and the ligand is capable of forming a stable bond to a support only when the probe is unbound to target.

Similarly, by way of example, background capture procedures featuring multiple probes in conjunction with target capture include two probes. A first target capture probe, having an unlabeled ligand capable of binding to a first support is used to capture the target and a second background capture probe, having a label moiety capable of detection includes a second ligand capable of binding to a second background support. Background capture is a valuable supplement to target capture for enhancing the signal to noise data of an assay.

The following sets forth a typical background capture protocol using a first target capture probe A532 and a second background capture probe A726 and a target enterotoxin gene elt AI. Those skilled in the art will recognize that the probes used for demonstration purposes are merely a matter of choice. Other probes could be used also.

The probe A532 was tailed with approximately 100 dA residues capable of reversibly binding to $dT_{10}$ covalently linked magnetic beads for initial target capture and $dT_{3000}$ nonspecifically bound to nitrocellulose for a final target capture. The probe A726 was end labeled with the random addition of approximately three residues of $^{32}$P-dC and $^{32}$P-dG to the 3' end with terminal transferase. The probe A726 is capable of binding to dC-cellulose when the probe is not hybridized to target.

A solution containing the target-first and second-probe-complex and potentially containing unbound second probe is mixed with dC-cellulose and the temperature of the mixture maintained at 37° C. The temperature, 37° C., is higher than the dissociation temperature of $dG_7$ with oligo dC, preventing binding of the target-first and second-probe-complex to the dC-cellulose. The temperature is also lower than the dissociation temperature of $dG_{10}$ with oligo dC to promote binding of unbound second probe having a dG tail to the dC-cellulose. Additionally, the target-first and second probe complex is sterically hindered to a greater degree in its approach to the dC-cellulose support than unbound second probe. The dC-cellulose containing the second probe A726 is removed by centrifugation, however, those skilled in the art will appreciate that other methods such as filtration may be used as well. The remaining eluate contains target-first and second probe complexes and a reduced concentration of unbound labeled second probe A726.

G. Examples

Individuals skilled in the art will recognize that the typical protocols for retrievable support preparation, probe preparation, target capture and background capture are capable of modification to suit special needs and purposes. The following examples incorporate the typical procedures outlined above unless otherwise noted.

Example 1

Target Capture and Assay Using Magnetic Bead

A target capture assay was performed with two probes and a magnetic bead retrievable support. The target included the Xba 1-Hind III fragment of the enterotoxigenic gene elt Al. A first probe included an A532 thirtimer oligonucleotide probe which was tailed with 130 unlabeled dA residues capable of binding to the $dT_{10}$ residues of the magnetic beads support. A second probe included an A483 thirtimer oligonucleotide probe capable of binding to the same target 20 nucleotides downstream from the site of hybridization of the first probe. The second probe was labeled by tailing the thirtimer oligonucleotide with $^{32}$P-dCTP and $^{32}$P-dGTP to a specific radioactivity of $10^{10}$ DPM/microgram.

The tailed first probe and the labeled second probe were incubated at 65° C. for 15 minutes in 1.4M sodium chloride with various quantities of heat denatured 475 mer restriction fragments of the tox gene. As a nonspecific binding background control, the tailed first probe and labeled second probe were incubated in identical solutions in the absence of any target. As specific binding controls, two additional reaction mixtures were formed. One reaction mixture included the tailed first probe and the unlabeled second probe incubated with four micrograms of denatured E. coli DNA, and a second reaction mixture of the tailed first probe and the labeled second probe incubated in ten micrograms of denatured human DNA in identical reaction mixtures without any target DNA.

After a 15 minute hybridization period, the samples were incubated for five minutes with dT-derivized magnetic beads in 0.7 milliliters of 0.75 molar phosphate buffer (pH 6.8). The beads were magnetically immobilized and washed extensively as described previously. The target-probe complex was eluted from the beads at 60° C. in 0.6 milliliters of 0.20 molar phosphate buffer (pH 6.8). The first set of beads was separated from the eluate and the target probe complex. A second group of magnetic beads was added to the eluate and brought to binding conditions to capture the target and probe complex again. The second set of beads was washed and the target again eluted from the beads and the beads separated from the eluate.

A third set of beads was added to the eluate containing the target-probe complex and placed under binding conditions to allow the beads to once again capture the target-probe complex. The beads were then washed extensively and the target eluted from the beads as previously described. The beads were then separated from the eluate and the eluate passed through $dT_{3000}$-nylon into two millimeter square slots, capturing the target-probe complex.

The $dT_{3000}$ nylon membrane was prepared in which 2 µg $dT_{3000}$ was covalently bound to nylon using a hybri-slot apparatus (Betlesda Research Laboratory). Briefly, $dT_{3000}$ (Life Sciences) was dotted directly onto a nylon membrane such as Gene-Screen™ (New England Nuclear) in a salt-free Tris buffer. The membrane was dried at room temperature for 10 minutes, and then dried under an infrared lamp for an additional 10 minutes before cooling back to room temperature for another 10 minutes. The filter apparatus containing the nylon membrane was inverted on a uv-transilluminator (Fotodyne) and exposed to uv light for two minutes at 40 uW/cm$^2$ to cross-link the dT$_{3000}$ to the filter.

The dT$_{3000}$ membrane was prehybridized by sequentially passing the following solutions through the membrane:

(1) 1% SDS;

(2) 0.5 mg/ml BSA in 0.5% SDS; and, finally, (3) prehybridization buffer

The dT$_{3000}$-nylon potentially containing the target-probe complex was washed with 0.2 molar sodium phosphate and 5 millimolal EDTA. The nylon support was monitored overnight by audioradiography for the presence of the $^{32}$p label moieties of the second probe. Following audioradiography, the bands were cut out of the filter and counted in base scintillation fluid. The counts were 2100 and 1400 counts per minute in the solution containing three femtomoles of a restriction fragment containing the tox gene. Samples containing 30 attomoles of the restriction fragment containing the tox gene produced a count of 62 counts per minute.

A third sample containing no DNA produced seven counts per minute. A fourth sample containing ten micrograms of heat denatured human DNA produced 0 counts per minute. A fifth solution containing 4 micrograms of heat denatured E. coli DNA produced 7 counts per minute. The absolute sensitivity of the protocol was estimated to be 10$^{18}$ mole of tox gene. The overall efficiency of the recovery of labeled target-probe complex was estimated to be 1 to 2 percent of the input. The assay demonstrated good specificity. There is no more labeled probe in the samples containing human DNA or E. coli DNA than in the sample containing no DNA at all. Repetition of the experimental protocol has produced overall efficiency of capture of the target of almost 5 percent. The procedures reduced background from an initial level of 10$^{11}$ molecules of the labeled unhybridized probes to about 10$^4$ moles. The reduction and background represents a 7 log improvement which more than adequately compensates for the reduction and efficiency of capture.

Example 2

The present example features target capture with background capture. Target and background capture was effected using an unlabeled first target capture probe, A532 as described in target capture, and a second labeled background capture probe A726.

First, 160 ng/ml dA-tailed A532 and 40 ng/ml $^{32}$P-labeled probe A726 were combined to form a probe mix. The probe mix was added to 5 μl of bacterial extract containing various amounts of enterotoxigenic gene. The extract-probe mix was incubated at 22° C. for 15 minutes.

After a fifteen minute hybridization period, the samples were diluted with ten volumes of prehybridization buffer incubated for five minutes with dT-derived magnetic beads in 0.7 ml of 0.75M phosphate buffer (pH 6.8) to effect target capture. The beads were magnetically immobilized and washed extensively. The target-first and second probe complex was eluted from the first support as previously described and the first solid support removed.

Next, the eluate containing the target-first and second-probe-complex and potentially containing unbound second probe was mixed with dC-cellulose and the temperature of the mixture maintained at 37° C. The temperature 37° C. is higher than the dissociation temperature of dG$_7$ with oligo dC to prevent binding of the target-first and second-probe-complex to the dC-cellulose. The temperature was also maintained lower than the dissociation temperature of dG$_{10}$ with oligo dC to promote binding of unbound second probe having a dG$_{10}$ tail to the dC-cellulose. The target-first and second probe complex is sterically hindered to a greater degree in its approach to the dC-cellulose support than unbound second probe. The dC-cellulose was removed by centrifugation, however, those skilled in the art will appreciate that other methods such as filtration may be used as well.

The remaining eluate was passed trough a 0.2 micron acrodisc (Gelman) to remove magnetic and celulite fines. Then, the eluate was passed through nitrocellulose filters containing dT$_{3000}$ at 22° C. The nitrocellulose effected final target capture.

Table 2 sets forth below the application of background capture:

TABLE 2

| Step | Signal (CPM) | Noise (CPM) |
|---|---|---|
| First Experiment | | |
| Before Target Capture | (unknown) | 200,000 |
| After Target Capture | 1058 | 231 |
| After Background Capture | 495 | 25 |
| After Filtration | 395 | <1 |
| Second Experiment | | |
| Before Target Capture | (unknown) | 400,000 |
| After Target Capture | 1588 | 642 |
| After Background Capture (Filtration step was not performed) | 1084 | 69 |

The removal of noise to less than 1 cpm allows the detection of very small quantities of target within a sample. As little as 10$^{-18}$ moles of target have been detected which is within the range necessary for clinical applications.

One round of target capture removed about 3 logs of background. One round of background capture removed 1 log of background not already removed by the primary target capture. Final target capture by filtration (a second round of target capture) removed 2 logs of background not removed by either of the first two steps. Target and background capture methods work independently to reduce backgrounds by about 6 logs in this example. Background capture appears to work better when applied after a first target capture. Apparently, background capture is much more sensitive to impurities in the sample than target capture.

The combination of background capture following target capture produces a greater benefit than either applied alone.

Although the foregoing examples recite radioactive label moieties, it is expected that the present procedure would have its greatest impact on assay procedures utilizing non-radioactive label moieties. In particular, the present invention would be applicable to luminescent label moieties including fluorescent and chemiluminescent agents. Suitable fluorescent labels include, by way example without limitation, fluoroscein, pyrene, acridine, sulforhodamine, eosin, erythrosin, and derivatives thereof. Suitable chemiluminescent agents include, by way of example without limitation, microperoxidase, luminol, isoluminol, glucose oxidase, acridinium esters and derivatives thereof.

Example 3

The following example features nonradioactive label moieties and multiple rounds of target capture from spiked biological media. The spiked biological media resembles samples which would be obtained clinically in a medical setting.

Cell extracts of enterotoxigenic *E. coli* and wild type *E. coli* were prepared as previously described. To measure the sensitivity of the detection of tox genes in an environment analogous to a clinical setting, extract containing toxigenic bacteria was diluted with the extract containing the wild type *E. coli* as previously described.

The following materials were obtained from anonymous donors: human stool sample, cow's milk, human saliva, human phlegm, human whole blood, human serum, human urine and human semen. Clinical-type samples were solubilized over a time period of ten minutes. The stool sample, due to its solid nature, was solubilized in a solution of 5M GuSCN, 0.3M Tris-HCl (pH 7.4), 0.1M EDTA (pH 7), 1% betamercaptoethanol. Following solubilization, aliquots of the sample were made and each aliquot was spiked with a known quantity of either toxigenic *E. coli* or wild type *E. coli*. The mixture was then passed through a crude filtration (Biorad Econocolumn) and heated to 100° C. for five minutes.

The remainder of the samples were more liquid in nature and were handled differently than stool. Liquid samples were added to solid GuSCN to make the final concentration 5M. The solid GuSCN also contained sufficient Tris-HCl, EDTA, and betamercaptoethanol to make the final concentrations the same as in the stool example. Next, aliquots of the samples were made and each aliquot was spiked with a known amount of toxigenic *E. coli* or wild type *E. coli*. The mixture was passed through a crude filtration (Biorad Econocolumn and heated to 100° C. for five minutes.

The preparation of probes in Example 3 differs from previous examples. A first capture probe was generated with the plasmid pBR322. The plasmid was restricted with Hha I and Hae III and plasmid fragments were tailed with about 100 dA residues with terminal transferase. The target plasmid contains extensive homology with pBR322 (Spicer and Noble, JBC 257, 5716–21). Thus, first capture probes were generated from multiple fragments of both strands of the plasmid pBR322 in relatively large quantities.

A second label probe was made to combine specifically to the target enterotoxin gene. The second label probe was generated from an EcoRI-Hind III restriction fragment of the elt Al gene cloned into bacteriophage M13mp18. The *E. coli* HB101 was infected with the bacteriophage and grown to midlog phase. The *E. coli* were harvested, and the bacteriophage were isolated. Bacteriophage was nick-translated with biotinylated dCTP (Enzo Biochemicals) using a stock nick-translation kit available from Bethesda Research Laboratories. Approximately five percent of the nucleotides were replaced with biotinyl nucleotides to form a biotin-labeled second probe.

A probe mix was made by combining 8 μg/ml of the second M13-tox probe with 4 μg/ml of the first dA-tailed first probe in 20 mM Tris-HCl (pH 7.4) and 2 mM EDTA. The probe mix was heated to 100° C. for ten minutes to denature the probes.

One volume of the probe mix was mixed with one volume of sample of the dilution series to form a hybridization mixture. The hybridization mixture was maintained under hybridization conditions at 57° C. for fifteen minutes. The hybridization mixtures were subsequently diluted with ten volumes of blocking buffer (0.75M sodium phosphate, pH 6.8, 0.5% sodium lauryl sarcosine, 10 mg/ml *E. coli* DNA, 0.5 mg/ml bovine serum albumin (BSA-nuclease free) and 5 mM EDTA). To the hybridization mixture were added $dT_{10}$ derivized magnetic beads prepared as previously described. Hybridization conditions were maintained approximately one minute at 22° C. The beads were then separated from the hybridization mixture by magnetically immobilizing the beads. The beads were washed twice during a fifteen minute time interval to remove impurities in the biological specimen and unhybridized biotin labeled second probe.

Next, in a time period of approximately one minute, the first and second probe-target complex was eluated from the magnetic beads at 65° C. in blocking buffer. The eluate and the first beads were separated.

In a time period of approximately seven minutes, the first and second probe-target complex was releasibly bound to a second set of beads and again released. A second set of $dT_{10}$ derivized beads were then added to the diluted eluate and hybridization conditions maintained for approximately one minute at 22° C. The beads were then washed and resuspended in blocking buffer. The bead blocking buffer mixture was then brought to 65° C. to release the first and second probe-target complex.

Over a time period of five minutes, final capture of the first and second probe-target complex on nitrocellulose was effected. The eluate from the second beads filtered through a Gelman acrodisc (0.2 micron). The eluate containing the first and second probe-target complex was then passed through a $dT_{3000}$ nitrocellulose filter (prehybridized with blocking buffer) at 22° C.

In a time period of approximately thirty minutes the filter was further processed to detect the biotin labels of the second probe. Buffer compositions used in detection are identified below in Table 3.

TABLE 3

Detection Buffers

| Buffer Number | Composition |
|---|---|
| 1 | 1 M NaCl, 0.1 M Tris-Hcl (pH 7.4), 5 mM $MgCl_2$, 0.1% Tween-20 |
| 1a | No. 1 with 5 mg/ml BSA, 10 micrograms/ml *E. coli* DNA |
| 2 | No. 1 with 5% BSA, 0.5% Tween-20 |
| 3 | 0.1 M NaCl, 0.1 M Tris-Hcl (pH 9.5), 50 mM $MgCl_2$ |

First, the filter carrying the first and second probe-target complex, was incubated for approximately five minutes in detection buffer No. 2. Next, the filter was incubated for five minutes in a 1:200 dilution of strepavidin-alkaline phosphatase (Bethesda Research Laboratories) in detection buffer No. 1a. Thereafter, the filter was washed three times in one minute in detection buffer No. 1 and then washed twice in one minute in detection buffer No. 3.

Next, 5-Bromo-4-chloro-3-indolyl phosphate (BCIP) and nitroblue tetrazolium (NBT) (Kierkegaard and Perry) were diluted twelve times in detection buffer No. 3, and filtered through a 0.2 micron acrodisc. The diluted BCIP and NBT solution was added to the filter and color allowed to develop for fifteen minutes at 37° C.

Next, the filter was incubated in 50 mM Tris-HCl (pH 7.4) and 10 mM EDTA for one minute to stop the reaction.

Sensitivity was determined visually on the filter or by densitometric scanning on a CS 930 (Shimadzu Scientific).

The steps in the present method are outlined below in Table 4.

TABLE 4

| Step Number | | Time Required (min.) | Cumulative Timed (min.) |
|---|---|---|---|
| 1. | Dissolution of biological sample; denaturation of DNA | 10 | 10 |
| 2. | Add labeled and unlabeled probes; hybridize in solution at 57° C. | 15 | 25 |
| 3. | Capture probe-target complex on magnetic beads | 1 | 26 |
| 4. | Wash magnetic beads to remove impurities in the biological specimen and hybridization backgrounds | 15 | 41 |
| 5. | Elute the probe-target complex | 1 | 42 |
| 6. | Repeat steps 3–5 on a second set of beads (except abbreviate the washes) | 7 | 49 |
| 7. | Bind the probe-target complex to $dT_{3000}$-nitrocellulose | 5 | 54 |
| 8. | Incubate filter in blocking buffer | 5 | 59 |
| 9. | Bind streptavidin-alkaline phosphatase | 5 | 64 |
| 10. | Wash | 5 | 69 |
| 11. | Add dyes to detect enzyme | 15 | 84 |
| 12. | Quench reaction | 1 | 85 |

Although Table 4 set forth an example wherein the elapsed time is just over one hour, the procedure is capable of modification and can be performed in shorter times. Nonradioactive probe assays of comparable sensitivity may require twelve hours to several days and require extensive sample preparation.

The sensitivity of the present assay is set forth in Table 5 below:

TABLE 5

| | Sensitivity Level | |
|---|---|---|
| Biological Specimen | Concentration in the Hybridization Mixture | Number of Bacteria |
| bacterial extract alone | | 1500 |
| human stool | 2.5% (w/v) | 2000 |
| cow's milk | 12.5% (v/v) | 3000 |
| human saliva | 12.5% (v/v) | 3000 |
| human urine | 12.5% (v/v) | 9000 |
| human semen | 2.5% (v/v) | 9000 |
| human blood | 12.5% (v/v) | 9000 |
| human serum | 12.5% (v/v) | 9000 |
| human phlegm | 12.5% (v/v) | 9000 |

Further, the present procedures are capable of further modifications to improve sensitivities. For example, a combination of thermal elution and chemical elution in multiple captured release cycles produces a signal to noise ratio five times better than single forms of elution, either multiple thermal elutions alone or multiple chemical elutions alone.

Applying the same releasing or elution procedure tends to release the same background from the support. However, applying different releasing conditions tends to retain background on the support that would otherwise be eluted. It is unlikely that background will behave identically to target under two physically or chemically distinct conditions.

A typical chemical elution of target-probe complexes on magnetic beads includes bringing beads in contact for one minute at room temperature. Examples of thermal elutions have been described previously.

The ability to detect bacteria would also be improved by directing probes to ribosomal RNA sequences. Ribosomal RNA sequences present a thousand fold increase in target per cell as compared to genomic DNA and clinically significant plasmid DNA.

Thus, the present invention features a method for target capture and background reduction and apparatus for performing affinity assays. While preferred embodiments have been illustrated and described, it is understood that the present invention is capable of variation and modification and, therefore, should not be limited to the precise details set forth, but should include such changes and alterations that fall within the purview of the following claims.

I claim:

1. A method for assaying a sample for target nucleic acid comprising the steps of:
   (a) contacting the sample with reagent comprising a first nucleic acid probe and a second nucleic acid probe which bind to the target to form a probe-target complex and wherein said second nucleic acid probe comprises a label;
   (b) contacting the sample with a support which binds to the first nucleic acid probe of the probe-target complex;
   (c) substantially separating the support and bound probe-target complex from the sample;
   (d) contacting the support and bound probe-target complex with a second medium;
   (e) releasing the probe-target complex into the second medium;
   (f) substantially separating the support from the second medium; and
   (g) monitoring the probe-target complex for the presence of the second nucleic acid probe indicating the presence of target.

2. The method of claim 1 wherein the support is substantially dispersed in each of said sample and said second medium.

3. The method of claim 1 wherein said support comprises beads.

4. The method of claim 3 wherein said beads are magnetic.

5. The method of claim 1 further comprising the steps of:
   (a) contacting the second medium with additional support which binds to the first nucleic acid probe of the probe-target complex; and
   (b) substantially separating said support and bound probe-target complex from said second medium.

6. The method of claim 5 further comprising the steps of:
   (a) contacting said support and bound probe-target complex with a third medium;
   (b) releasing the probe-target complex into the third medium; and
   (c) substantially separating said support from said third medium.

7. The method of claim 6 wherein the additional support is substantially dispersed in each of the second medium and the third medium.

8. The method of claim 6 further comprising an additional cycle of capture and release of the probe-target complex.

9. A method for separating target nucleic acid in a sample from non-target nucleic acid in the sample comprising the steps of:
   (a) contacting the sample with reagent comprising a first nucleic acid probe which binds to the target to form a probe-target complex but does not bind to non-target nucleic acid;

(b) contacting the sample with a support which binds to the first nucleic acid probe of the probe-target complex;

(c) substantially separating the support and bound probe-target complex from the sample and non-target nucleic acid;

(d) contacting the support and bound probe-target complex with a second medium;

(e) releasing the target from the support and bound first nucleic acid probe; and (f) substantially separating the support and bound first nucleic acid probe from the second medium.

10. The method of claim 9 wherein the support is substantially dispersed in each of the sample and the second medium.

11. The method of claim 9 wherein the support comprises beads.

12. The method of claim 11 wherein the beads are magnetic.

13. The method of claim 9 further comprising the steps of:

(a) contacting said second medium with additional first nucleic acid probe which binds to the target to form probe-target complex;

(b) contacting the second medium with additional support which binds to the first nucleic acid probe of the probe-target complex; and (c) substantially separating the support and bound probe-target complex.

14. The method of claim 13 further comprising the steps of:

(a) contacting said support and bound probe-target complex with a third medium;

(b) releasing the target from the support and bound first nucleic acid probe; and (c) substantially separating the support and bound first nucleic acid probe from the third medium.

15. The method of claim 14 wherein the support is substantially dispersed in the sample and the second and third media.

16. The method of claim 15 wherein the support comprises magnetic beads.

17. The method of claim 14 further comprising at least one additional cycle of target capture and release.

18. A method for assaying a sample for target nucleic acid comprising the steps of:

(a) contacting the sample with reagent comprising a first nucleic acid probe which binds to the target to form a probe-target complex;

(b) contacting the sample with a support which binds to the first nucleic acid probe of the probe-target complex;

(c) substantially separating the support and bound probe-target complex from the sample;

(d) contacting the support and bound probe-target complex with a second medium;

(e) releasing the target from the support and bound first nucleic acid probe;

(f) substantially separating the support and bound first nucleic acid probe from the second medium; and (g) monitoring the second medium for the presence of target.

19. A method for determining the presence of a target nucleic acid in a sample comprising the steps of:

(a) contacting the sample with reagent comprising a first nucleic acid probe which binds to the target to form a probe-target complex;

(b) contacting the sample with a support which binds to the first nucleic acid probe of the probe-target complex;

(c) substantially separating the support and bound probe-target complex from the sample;

(d) contacting the support and bound probe-target complex with a second medium;

(e) releasing the target from the support and bound first nucleic acid probe;

(f) substantially separating the support and bound first nucleic acid probe from the second medium such that the target remains in the second medium; and (g) detecting the presence of target present in the second medium.

20. A method for assaying a sample for target nucleic acid comprising the steps of:

(a) contacting the sample with reagent comprising a first nucleic acid probe and at least one second nucleic acid probe which bind to the target to form a probe-target complex;

(b) contacting the sample with a support which binds to the first nucleic acid probe of the probe-target complex;

(c) substantially separating the support and bound probe-target complex from the sample;

(d) contacting the support and bound probe-target complex with a second medium;

(e) releasing the probe-target complex into the second medium;

(f) substantially separating the support from the second medium; and (g) monitoring the probe-target complex for the presence of the second nucleic acid probe indicating the presence of target.

* * * * *